(12) United States Patent
Roll et al.

(10) Patent No.: US 11,547,542 B2
(45) Date of Patent: *Jan. 10, 2023

(54) MINIMALLY INVASIVE IMPLANT AND METHOD

(71) Applicant: Boston Scientific Scimed, Inc., Maple Grove, MN (US)

(72) Inventors: Jessica L. Roll, Phoenix, AZ (US); John Fritz Otte, St. Anthony, MN (US); Mona N. Dahdah, West St. Paul, MN (US); Brian G. Fischer, Minneapolis, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 105 days.

This patent is subject to a terminal disclaimer.

(21) Appl. No.: 16/710,833

(22) Filed: Dec. 11, 2019

(65) Prior Publication Data
US 2020/0113664 A1    Apr. 16, 2020

Related U.S. Application Data

(63) Continuation of application No. 15/618,102, filed on Jun. 8, 2017, now Pat. No. 10,537,416, which is a (Continued)

(51) Int. Cl.
*A61F 2/00* (2006.01)
*A61B 17/04* (2006.01)
(Continued)

(52) U.S. Cl.
CPC ........ *A61F 2/0045* (2013.01); *A61B 17/0401* (2013.01); *A61B 17/06109* (2013.01);
(Continued)

(58) Field of Classification Search
CPC .... A61F 2/0004; A61F 2/0031; A61F 2/0036; A61F 2/0045; A61F 2/0063; A61B 17/0401

See application file for complete search history.

(56) References Cited

U.S. PATENT DOCUMENTS 2,738,790 A   3/1956   Todt, Sr. et al.
3,124,136 A   3/1964   Usher
(Continued)

FOREIGN PATENT DOCUMENTS

AU   2002241673 B2   8/2005
CA      2404459 C    8/2005
(Continued)

OTHER PUBLICATIONS

AlloSource Product Literature, 11 pages.
(Continued)

*Primary Examiner* — John P Lacyk
(74) *Attorney, Agent, or Firm* — Brake Hughes Bellermann LLP

(57) ABSTRACT

Apparatus and methods are provided for treating urinary incontinence, fecal incontinence, and other pelvic defects or dysfunctions, in both males and females, using one or more lateral implants to reinforce the supportive tissue of the urethra. The implants can be configured as a sling device having at least one extension arm and a tissue support portion having an eyelet, wherein a portion of the at least one extension arm is adapted to slide through and adjustably attach with the eyelet.

20 Claims, 17 Drawing Sheets

Related U.S. Application Data continuation of application No. 14/697,525, filed on Apr. 27, 2015, now Pat. No. 9,867,685, which is a continuation of application No. 13/335,472, filed on Dec. 22, 2011, now Pat. No. 9,017,243, which is a continuation-in-part of application No. 13/060,467, filed as application No. PCT/US2009/054909 on Aug. 25, 2009, now Pat. No. 8,968,181.

(60) Provisional application No. 61/426,117, filed on Dec. 22, 2010, provisional application No. 61/091,586, filed on Aug. 25, 2008.

(51) Int. Cl.
*A61B 17/06* (2006.01)
*A61B 17/00* (2006.01)

(52) U.S. Cl.
CPC .............. *A61B 2017/00805* (2013.01); *A61B 2017/0409* (2013.01); *A61B 2017/0412* (2013.01); *A61B 2017/0414* (2013.01); *A61B 2017/0417* (2013.01); *A61B 2017/0464* (2013.01); *A61F 2220/0016* (2013.01); *A61F 2250/0097* (2013.01)

(56) References Cited

U.S. PATENT DOCUMENTS

| | | |
|---|---|---|
| 3,182,662 A | 5/1965 | Shirodkar |
| 3,311,110 A | 3/1967 | Singerman et al. |
| 3,384,073 A | 5/1968 | Winkle, Jr. |
| 3,472,232 A | 10/1969 | Earl |
| 3,580,313 A | 5/1971 | Mcknight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendroff |
| 4,128,100 A | 12/1978 | Wendroff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | OKeeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Farrer Velazquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig et al. |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,647,836 A | 7/1997 | Blake, III et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. et al. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses et al. |
| 6,099,551 A | 8/2000 | Gabbay |
| 6,099,552 A | 8/2000 | Adams |
| 6,106,545 A | 8/2000 | Egan |

(56) References Cited

U.S. PATENT DOCUMENTS

| | | |
|---|---|---|
| 6,110,101 A | 8/2000 | Tihon et al. |
| 6,117,067 A | 9/2000 | GilVernet |
| 6,127,597 A | 10/2000 | Beyar et al. |
| 6,168,611 B1 | 1/2001 | Rizvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar et al. |
| 6,352,553 B1 | 3/2002 | Van Der Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory et al. |
| 6,582,443 B2 | 6/2003 | Cabak et al. |
| 6,592,515 B2 | 7/2003 | Thierfelder et al. |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman |
| 6,691,711 B2 | 2/2004 | Raz et al. |
| 6,699,175 B2 | 3/2004 | Miller |
| 6,702,827 B1 | 3/2004 | Lund et al. |
| 6,752,814 B2 | 6/2004 | Gellman et al. |
| 6,755,781 B2 | 6/2004 | Gellman |
| 6,802,807 B2 | 10/2004 | Anderson et al. |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski et al. |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin et al. |
| 7,025,772 B2 | 4/2006 | Gellman et al. |
| 7,037,255 B2 | 5/2006 | Inman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jacquetin |
| 7,175,591 B2 | 2/2007 | Kaladelfos |
| 7,198,597 B2 | 4/2007 | Siegel et al. |
| 7,226,407 B2 | 6/2007 | Kammerer et al. |
| 7,226,408 B2 | 6/2007 | Harai et al. |
| 7,229,404 B2 | 6/2007 | Bouffier |
| 7,229,453 B2 | 6/2007 | Anderson et al. |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac et al. |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin et al. |
| 7,410,460 B2 | 8/2008 | Benderev |
| 7,413,540 B2 | 8/2008 | Gellman et al. |
| 7,422,557 B2 | 9/2008 | Arnal et al. |
| 7,431,690 B2 | 10/2008 | Merade et al. |
| 7,494,495 B2 | 2/2009 | Delorme et al. |
| 7,500,945 B2 | 3/2009 | Cox et al. |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Raff et al. |
| 7,753,839 B2 | 7/2010 | Siegel et al. |
| 7,762,942 B2 | 7/2010 | Neisz et al. |
| 7,766,926 B2 | 8/2010 | Bosley, Jr. et al. |
| 7,789,821 B2 | 9/2010 | Browning |
| 8,968,181 B2 | 3/2015 | Roll et al. |
| 9,017,243 B2 | 4/2015 | Roll et al. |
| 9,687,685 B1 | 6/2017 | Chmielewski |
| 9,918,816 B2 | 3/2018 | Roll et al. |
| 10,537,416 B2 * | 1/2020 | Roll ............... A61B 17/0401 |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz et al. |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0176875 A1 | 9/2003 | Anderson et al. |
| 2004/0015057 A1 | 1/2004 | Rocheleau et al. |
| 2004/0039453 A1 | 2/2004 | Anderson et al. |
| 2004/0073235 A1 | 4/2004 | Lund et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |

(56) References Cited

U.S. PATENT DOCUMENTS

| | | |
|---|---|---|
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt |
| 2006/0015010 A1 | 1/2006 | Jaffe et al. |
| 2006/0028828 A1 | 2/2006 | Phillips |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0173237 A1 | 8/2006 | Jacquetin |
| 2006/0195007 A1 | 8/2006 | Anderson et al. |
| 2006/0195011 A1 | 8/2006 | Arnal et al. |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi et al. |
| 2007/0015953 A1 | 1/2007 | MacLean |
| 2007/0078295 A1 | 4/2007 | Landgrebe et al. |
| 2007/0173864 A1 | 7/2007 | Chu |
| 2008/0039678 A1 | 2/2008 | Montpetit et al. |
| 2008/0045782 A1 | 2/2008 | Jimenez |
| 2008/0300607 A1 | 12/2008 | Meade et al. |
| 2009/0005634 A1 | 1/2009 | Rane et al. |
| 2009/0012353 A1 | 1/2009 | Beyer et al. |
| 2009/0221868 A1 | 9/2009 | Evans |
| 2011/0112357 A1 | 5/2011 | Chapman et al. |
| 2015/0164626 A1 | 6/2015 | Roll et al. |
| 2015/0238297 A1 | 8/2015 | Roll et al. |

FOREIGN PATENT DOCUMENTS

| | | |
|---|---|---|
| DE | 2305815 A1 | 8/1974 |
| DE | 1220283 C2 | 5/1994 |
| DE | 19544162 C1 | 4/1997 |
| DE | 20016866 U1 | 12/2000 |
| DE | 10211360 A1 | 10/2003 |
| EP | 248544 A1 | 12/1987 |
| EP | 470308 A1 | 2/1992 |
| EP | 632999 A1 | 1/1995 |
| EP | 643945 A2 | 3/1995 |
| EP | 650703 A1 | 5/1995 |
| EP | 1093758 A1 | 4/2001 |
| EP | 1060714 A3 | 10/2002 |
| EP | 1342450 B1 | 1/2007 |
| EP | 2323586 A1 | 5/2011 |
| FR | 2787990 A1 | 7/2000 |
| FR | 2852813 A1 | 10/2004 |
| GB | 2268690 A | 1/1994 |
| GB | 2353220 A | 2/2001 |
| IT | RM980239 A1 | 10/1999 |
| JP | 2001511686 A | 8/2001 |
| SU | 1225547 A1 | 4/1986 |
| SU | 1342486 A1 | 10/1987 |
| WO | 1993/017635 A1 | 9/1993 |
| WO | 1993/019678 A2 | 10/1993 |
| WO | 1995/011631 A1 | 5/1995 |
| WO | 1995/025469 A1 | 9/1995 |
| WO | 1997/016121 A1 | 5/1997 |
| WO | 1997/030638 A1 | 8/1997 |
| WO | 1997/047244 A1 | 12/1997 |
| WO | 1998/019606 A1 | 5/1998 |
| WO | 1998/035606 A2 | 8/1998 |
| WO | 1998/035616 A1 | 8/1998 |
| WO | 1998/035632 A1 | 8/1998 |
| WO | 1998/042261 A1 | 10/1998 |
| WO | 1998/053746 A1 | 12/1998 |
| WO | 1999/016381 A1 | 4/1999 |
| WO | 1999/037217 A1 | 7/1999 |
| WO | 1999/052450 A1 | 10/1999 |
| WO | 1999/053844 A1 | 10/1999 |
| WO | 1999/059477 A1 | 11/1999 |
| WO | 2000/013601 A1 | 3/2000 |
| WO | 2000/018319 A1 | 4/2000 |
| WO | 2000/027304 A1 | 5/2000 |
| WO | 2000/040158 A2 | 7/2000 |
| WO | 2000/057812 A1 | 10/2000 |
| WO | 2000/064370 A1 | 11/2000 |
| WO | 2000/066030 A1 | 11/2000 |
| WO | 2000/074594 A1 | 12/2000 |
| WO | 2000/074613 A1 | 12/2000 |
| WO | 2000/074633 A2 | 12/2000 |
| WO | 2001/006951 A1 | 2/2001 |
| WO | 2001/026581 A1 | 4/2001 |
| WO | 2001/039670 A1 | 6/2001 |
| WO | 2001/045588 A1 | 6/2001 |
| WO | 2001/045589 A1 | 6/2001 |
| WO | 2001/056499 A1 | 8/2001 |
| WO | 2002/028312 A1 | 4/2002 |
| WO | 2002/028315 A2 | 4/2002 |
| WO | 2002/030293 A1 | 4/2002 |
| WO | 2002/032284 A2 | 4/2002 |
| WO | 2002/034124 A2 | 5/2002 |
| WO | 2002/038079 A2 | 5/2002 |
| WO | 2002/039890 A2 | 5/2002 |
| WO | 2002/058563 A1 | 8/2002 |
| WO | 2002/062237 A1 | 8/2002 |
| WO | 2002/069781 A2 | 9/2002 |
| WO | 2002/071953 A2 | 9/2002 |
| WO | 2002/078552 A1 | 10/2002 |
| WO | 2002/089704 A2 | 11/2002 |
| WO | 2003/017848 A1 | 3/2003 |
| WO | 2003/028585 A2 | 4/2003 |
| WO | 2003/037215 A2 | 5/2003 |
| WO | 2003/041613 A1 | 5/2003 |
| WO | 2003/047435 A1 | 6/2003 |
| WO | 2003/068107 A1 | 8/2003 |
| WO | 2003/075792 A1 | 9/2003 |
| WO | 2003/092546 A2 | 11/2003 |
| WO | 2003/096929 A1 | 11/2003 |
| WO | 2004/012626 A1 | 2/2004 |
| WO | 2004/016196 A2 | 2/2004 |
| WO | 2004/017862 A2 | 3/2004 |
| WO | 2004/034912 A1 | 4/2004 |
| WO | 2005/037132 A2 | 4/2005 |
| WO | 2005/079702 A1 | 9/2005 |
| WO | 2005/122954 A1 | 12/2005 |
| WO | 2006/015031 A2 | 2/2006 |
| WO | 2006/108145 A1 | 10/2006 |
| WO | 2007/011341 A1 | 1/2007 |
| WO | 2007/014241 A1 | 2/2007 |
| WO | 2007/016083 A1 | 2/2007 |
| WO | 2007/027592 A1 | 3/2007 |
| WO | 2007/059199 A2 | 5/2007 |
| WO | 2007/081955 A1 | 7/2007 |
| WO | 2007/097994 A2 | 8/2007 |
| WO | 2007/137226 A2 | 11/2007 |
| WO | 2007/146784 A2 | 12/2007 |
| WO | 2007/149348 A2 | 12/2007 |
| WO | 2007/149555 A2 | 12/2007 |
| WO | 2008/057261 A2 | 5/2008 |
| WO | 2008/124056 A1 | 10/2008 |
| WO | 2009/005714 A2 | 1/2009 |
| WO | 2009/017680 A2 | 2/2009 |

OTHER PUBLICATIONS

Capio® CL Transvaginal Suture Capturing Device, The Capio CL Transvaginal Suture Capturing Device allows for a transvaginal suture fixation to Cooper's Ligament for Sling Procedures, 2002, 8 pages.

Comparison of Tissue Reaction of Monofilament and Multifilament Polypropylene Mesh—A Case report, Tyco Healthcare, United States Surgical, 4 pages.

Gynecare TVT Tension-Free Support for Incontinence, The tension-free Solution to Female Incontinence, Gynecare Worldw[de, 2002, 6 pages.

(56) References Cited

OTHER PUBLICATIONS

IVS Tunneller, Australian Medical Design Breakthrough for GSI, mixed incontinence and vault prolapse, AMA Medical Products, 4 pages.
IVS Tunneller, AMA, 4 pages.
IVS Tunneller—A Universal instrument for anterior and posterior intra-vaginal tape placemen, TCO Healthcare, Aug. 2002, 4 pages.
LigiSure Atlas™, Tyco Healthcare, Valleylab®, 2 pages.
Intramesh L.I.F.T. Siliconized polyester, Cousin Biotech, 1 page.
Intramesh® L.I.F.T.® Polypropylene Less Invasive Free Tape, Cousin Biotech, 2 pages.
Mentor Porges, Uratape, ICS/IUGA Symp, Jul. 2002.
Readjustable REMEEX System, Neomedic International, 8 Pages.
SABRE™ Bioabsorbable Sling, Generation Now, Mentor, May 2002, 4 pages.
SABRE™ Surgical Procedure, Mentor, 2002, 6 pages.
The McGuire™ Suture Guide: A Single Use Instrument Designed for the Placement of a Suburethral Sling, Bard, 2001, 2 pages.
Urethrovaginal Fixation to Cooper's Ligament for Correction of Stress Incontinence, Cystocele, and Prolapse, Am. J. Obst. & Gyn, vol. 31, 1961, pp. 281-290.
UroMed Access Instrument System for the Sub-urethral Sling Procedure Catalog No. 120235, Directions for Use, 3 pages.
We're staying ahead of the curve, Introducing the IVS Tunneller Device for Tension Free Procedures, Tyco Healthcare, 2002, 3 pages.
Aldridge, Albert H., "Transplantation of Fascia for Relief of Urinary Stress Incontinence", American Journal of Obstetrics and Gynecology, vol. 44, 1948, pp. 398-411.
Amundsen et al., "Anatomical Correction of Vaginal Vault Prolapse by Uterosacral Ligament Fixation in Women who Also Require a Pubovaginal Sling", Journal of Urology, vol. 169, May 2003, pp. 1770-1774.
Araki et al., "The Loop-Loosening Procedure for Urination Difficulties After Stamey Spension of the Vesical Neck", Journal of Urology, 144, Aug. 1990, pp. 319-323.
Asmussen et al., "Simultaneous Urethro-Cystometry with a New Technique", Scand J Urol Nephrol, vol. 10, 1976, pp. 7-11.
Beck et al., "Treatment of Urinary Stress Incontinence With Anterior Colporrhaphy", Obstetrics and Gynecology, vol. 59, No. 3, Mar. 1982, pp. 269-274.
Benderev, Theodore V., "A Modified Percutaneous Outpatient Bladder Neck Suspension System", Journal of Urology, vol. 152, Dec. 1994, pp. 2316-2320.
Benderev, Theodore V., "Anchor Fixation and Other Modifications of Endoscopic Bladder Neck Suspension", Journal of Urology, 40, Nov. 1992, pp. 409-418.
Bergman et al., "Three Surgical Procedures for Genuine Stress Incontinence: Five-year Follow-up of a Prospective Randomized Study", Am J Obstet Gynecol, vol. 173, No. 1, Jul. 1995, pp. 66-71.
Blaivas, Jerry, "Commentary: Pubovaginal Sling Procedure", Experience with Pubovaginal Slings, 1990, pp. 93-101.
Blaivas et al., "Pubovaginal Fascial Sling for the Treatment of Complicated Stress Urinary Incontinence", Journal of Urology, 145, Jun. 1991, pp. 1214-1218.
Blaivas et al., "Type III Stress Urinary Incontinence: Importance of Proper Diagnosis and Treatment", 1984, pp. 173-475.
Boston Scientific, "Surgical Mesh Sling Kit", Advantage AT™, 2002, 6 pages.
Boyles et al., "Procedures for Urinary Incontinence in the United States", Am J Obstet Gynecol, vol. 189, No. 1, Jul. 2003, pp. 70-75.
Bryans, Fred E., "Marlex Gauze Hammock Sling Operation With Cooper's Ligament Attachment in the Management of Recurrent Urinary Stress Incontinence", American Journal of Obstetrics and Gynecology, vol. 133, Feb. 1979, pp. 292-294.
Cervigni et al., "The Use of Synthetics in the Treatment of Pelvic Organ Prolapse", Voiding Dysfunction and Female Urology, vol. 11, 2001, pp. 429-435.
Choe et al., "Gore-tex Patch Sling: 7 Years Later", Ucology, vol. 54, 1999, pp. 641-646.
Cook/OB GYN®, "Urogynecology", Copyright Cook Urological Inc., 1996, pp. 1-36.
Dargent et al., "Insertion of a Suburethral Sling Through the Obturator Membrane in the Treatment of Female Urinary Incontinence", Gynecol Obstet Fertil, vol. 30, 2002, pp. 576-582.
Das et al., "Laparoscopic Colpo-Suspension", The Journal of Urology, vol. 154, Sep. 1995, pp. 1119-1121.
Debodinance et al., "Tolerance of Synthetic Tissues in Touch With Vaginal Scars: Review to the Point of 287 Cases", European Journal of Obstetrics & Gynecology and Reproductive Biology, vol. 87, 1999, pp. 23-30.
Decter, Ross M., "Use of the Fascial Sling for Neurogenic Incontinence: Lessons Learned", The Journal of Urology, vol. 150, Aug. 1993, pp. 683-686.
Delancey, John, "Structural Support of the Urethra as It Relates to Stress Urinary Incontinence: The Hammock Hypothesis", Am J Obstet Gynecol, vol. 170, No. 6, Jun. 1994, pp. 1713-1723.
Delorme, Emmanuel, "Trans-obturator Sling: A Minimal Invasive Procedure to Treat Female Stress Urinary Incontinence", Progres en Urologie, vol. 11, 2001, pp. 1306-1313.
Diana et al., "Treatment of Vaginal Vault Prolapse with Abdominal Sacral Colpopexy Using Prolene Mesh", American Journal of Surgery, vol. 179, Feb. 2000, pp. 126-128.
Conquy, Dr. Sophie, "Le point sur l'incontinence urinaire", Expertise et Practiques en Urologie, No. 3 [Hospital Cochin, Paris], pp. 17-19.
Drutz et al., "Clinical and Urodynamic Re-evaluation of Combined Abdominovaginal Marlex Sling Operations for Recurrent Stress Urinary Incontinence", International Urogynecology Journal, vol. 1, 1990, pp. 70-73.
Eglin et al., "Transobturator Subvesical Mesh", Tolerance and short-term results of a 103 case continuous series, Gynecologie Obstetrique & Fertilite, vol. 31, Issue 1, Jan. 2003, pp. 14-19.
Enzelsberger et al., "Urodynamic and Radiologic Parameters Before and After Loop Surgery for Recurrent Urinary Stress Incontinence", Acta Obstet Gynecol Scand, vol. 69, 1990, pp. 51-54.
Eriksen et al., "Long-term Effectiveness of the Burch Colposuspension in Female Urinary Stress Incontinence", Acta Obstet Gynecol Scand, vol. 69, 1990, pp. 45-50.
Falconer et al., "Clinical Outcome and Changes in Connective Tissue Metabolism After Intravaginal Slingplasty in Stress Incontinence Women", International Urogynecology Journal, 1966, pp. 133-137.
Falconer et al., "Influence of Different Sling Materials of Connective Tissue Metabolism in Stress Urinary Incontinent Women", International Urogynecology Journal, Supp 2, 2001, pp. S19-S23.
Farnsworth, "Posterior Intravaginal Slingplasty (Infracoccygeal Sacropexy) for Sever Posthysterectomy Vaginal Vault Prolapse—A Preliminary Report on Efficacy and Safety", International Urogynecology Journal, vol. 13, 2002, pp. 4-8.
Farquhar et al., "Hysterectomy Rates in the United States 1990-1997", Obstetrics & Gynecology, vol. 99. No. 2, Feb. 2002, pp. 229-234.
Fidela, et al., "Pelvic Support Defects and Visceral and Sexual Function in Women Treated With Sacrospinous Ligament Suspension and Pelvic Reconstruction", Am J Obstet Gynecol, vol. 175, No. 6, Dec. 1996.
Flood, C.G., "Anterior Colporrhaphy Reinforce With Marlex Mesh for the Treatment of Cystoceles", International Urogynecology Journal, vol. 9, 1998, pp. 200-204.
Gilja et al., "A Modified Raz Bladder Neck Suspension Operation (Transvaginal Burch)", The Journal of Urology, vol. 153, May 1995, pp. 1455-1457.
Gittes, Ruben F., "No-incision Pubovaginal Suspension for Stress Incontinence", The Journal of Urology, vol. 138, Sep. 1987.
Guner et al., "Transvaginal Sacrospinous Colpopexy for Marked Uterovaginal and Vault Prolapse", International Journal of Gynec & Obstetrics, vol. 74, 2001, pp. 165-170.
Handa et al., "Banked Human Fascia Lata for the Suburethral Sling Procedure: A Preliminary Report", Obstetrics & Gynecology, vol. 88, No. 6, Dec. 1996, 5 pages.

(56) References Cited

OTHER PUBLICATIONS

Heit et al., "Predicting Treatment Choice for Patients With Pelvic Organ Prolapse", Obstetrics & Gynecology, vol. 101, No. 6, Jun. 2003, pp. 1279-1284.
Henriksson et al., "A Urodynamic Evaluation of the Effects of Abdominal Urethrocystopexy and Vaginal Sling Urethroplasty in Women With Stress Incontinence", Am J. Obstet Gynecol, vol. 131, No. 1, Mar. 1, 1978, pp. 77-82.
Hodgkinson et al., "Urinary Stress Incontinence in the Female", Department of Gynecology and Obstetrics, Henry Ford Hospital, vol. 10, No. 5, Nov. 1957, pp. 493-499.
Holschneider et al., "The Modified Pereyra Procedure in Recurrent Stress Urinary Incontinence: A 15-year Review", Obstetrics & Gynecology, vol. 83, No. 4, Apr. 1994, pp. 573-578.
Horbach et al., "Instruments and Methods, A Suburethral Sling Procedure With Polytetrafluoroethylene for the Treatment of Genuine Stress Incontinence in Patients With Low Urethral Closure Pressure", Obstetrics & Gynecology, vol. 71, No. 4, Apr. 1998, pp. 648-652.
Horbach, Nicollette, "Suburethral Sling Procedures", Genuine Stress Incontinence, Chapter 42, pp. 569-579.
Ingelman-Sunberg et al., "Surgical Treatment of Female Urinary Stress Incontinence", Contr. Gynec. Obstet., vol. 10, 1983, pp. 51-69.
IVS Tunneller, "ein universelles Instrument fur die Intra Vaginal Schlingenplastik", TCO Healthcare, 2001, 4 pages.
Jeffcoate et al., "The Results of the Aldridge Sling Operation for Stress Incontinence", Journal of Obstetrics and Gynaecology, 1956, pp. 36-39.
Jones et al., "Pelvic Connective Tissue Resilience Decreases With Vaginal Delivery, Menopause and Uterine Prolapse", Br J Surg, vol. 90, No. 4, Apr. 2003, pp. 466-472.
Julian, Thomas, "The Efficacy of Marlex Mesh in The Repair of Sever, Recurrent Vaginal Prolapse of the Anterior Midvaginal Wall", Am J Obstet Gynecol, vol. 175, No. 6, Dec. 1996, pp. 1472-1475.
Karram et al., "Chapter 19 : Surgical Treatment of Vaginal Vault Prolapse", Urogyn-cology and Reconstructive Pelvic Surgery, 1999, pp. 235-256.
Karram et al., "Patch Procedure: Modified Transvaginal Fascia Lata Sling For Recurrent For Severe Stress Urinary Incontinence", vol. 75, Mar. 1990, pp. 461-463.
Kersey, "The Gauze Hammock Sling Operation in the Treatment of Stress Incontinence", British Journal of Obstetrics and Gynaecology, vol. 90, Oct. 1983, pp. 945-949.
Klutke et al., "The Anatomy of Stress Incontinence: Magentic Resonance Imaging of the Female Bladder Neck and Urethra", The Journal of Urology, vol. 143, Mar. 1990, pp. 563-566.
Klutke et al., "The Promise of Tension-Free Vaginal Tape for Female SUI", Contemporary Urology, Oct. 2000, 7 pages.
Klutke et al., "Transvaginal Bladder Neck Suspension to Cooper's Ligament: A Modified Pereyra Procedure", Obstetrics & Gynecology, vol. 88, No. 2, Aug. 1996, pp. 294-296.
Korda et al., "Experience With Silastic Slings for Female Urinary Incontinence", Aust NZ J. Obstet Gynaecol, vol. 29, May 1989, pp. 150-154.
Kovac, S. Robert, "Follow-up of the Pubic Bone Suburethral Stabilization Sling Operation for Recurrent Urinary ncontinence (Kovac Procedure)", Journal of Pelvic Surgery, May 1999, pp. 156-160.
Kovac et al., "Pubic Bone Suburethral Stabilization Sling for Recurrent—Urinary Incontinence", Obstetrics & Gynecology, vol. 89, No. 4, Apr. 1997, pp. 624-627.
Kovac et al., "Pubic Bone Suburethral Stabilization Sling: A Long Term Cure for SUI?", Contemeorary OB/GYN, Feb. 1998, 10 pages.
Kovac, Stephen Robert, M.D., Cirriculum Vitae, Jun. 18, 1999, pp. 1-33.
Leach, Gary E., "Bone Fixation Technique for Transvaginal Needle Suspension", Urology vol. XXXI, No. 5, May 1988, pp. 388-390.

Leach et al., "Female Stress Urinary Incontinence Clinical Guidelines Panel Report on Surgical Management of Female Stress Urinary Incontinence", American Urological Association, vol. 158, Sep. 1997, pp. 875-880.
Lightenstein et al., "The Tension Free Hemioplasty", The American Journal of Surgery, vol. 157, Feb. 1989, pp. 188-193.
Loughlin et al., "Review of An 8-year Experience With Modifications of Endoscopic Suspension of the Bladder Neck for Female Stress Incontinence", The Journal of Urology, vol. 143, 1990, pp. 44-45.
Luber et al., "The Demographics of Pelvic Floor Disorders: Current Observations and Future Projections", Am J Obstet Gynecol, vol. 184, No. 7, Jun. 2001, pp. 1496-1503.
Mage, "Technique Chirurgicale, L'interpostion D'un Treillis Synthetique Dans La Cure Par Voie Vaginale Des Prolapsus Genitaux", J Gynecol Obstet Bioi Reprod, vol. 28, 1999, pp. 825-829.
Marchionni et al., "True Incidence of Vaginal Vault Prolapse—Thirteen Years of Experience", Journal of Reproductive Medicine, vol. 44, No. 8, Aug. 1999, pp. 679-684.
Marinkovic et al., "Triple Compartment Prolapse: Sacrocolpopexy With Anterior and Posterior Mesh Extensions", Br J Obstet Gynaecol, vol. 110, Mar. 2003, pp. 323-326.
Marshall et al., "The Correction of Stress Incontinence by Simple Vesicourethral Suspension", Surgery, Gynecology and Obstetrics, vol. 88, 1949, pp. 509-518.
Mascio, Valenzio C., "MITEK Brochure, Therapy of Urinary Stress Incontinence in Women Using Mitek Gill Anchors".
McGuire et al., "Abdominal Fascial Slings", Slings, Raz Female Urology, 1996, pp. 369-375.
McGuire, E J., "Abdominal Procedure for Stress Incontinence", Urol Clin North Am., vol. 12, No. 2, May 1985, pp. 285-290.
McGuire et al., "Experience With Pubovaginal Slings for Urinary Incontinence at the University of Michigan", Journal of Urology, vol. 138, 1987, pp. 90-93.
McGuire et al., "Pubovaginal Sling Procedure for Stress Incontinence", Journal of Urology, vol. 119, No. 1, 1978, pp. 82-84.
McGuire, Edward J., "The Sling Procedure for Urinary Stress Incontinence", Profiles in Urology, pp. 3-18.
McIndoe et al., "The Aldridge Sling Procedure in the Treatment of Urinary Stress Incontinence", Aust. N Z Journal of Obstet Gynecology, Aug. 1987, pp. 238-239.
McKiel et al., "Marshall-Marchetti Procedure: Modification", The Journal of Urology, vol. 96, No. 5, Dec. 1966, pp. 737-739.
Migliari, Roberto, "Tension-free Vaginal Mesh Repair for Anteriorvaginal Wall Prolapse", Eur Urol, vol. 38, Oct. 1999, pp. 151-155.
Migliari et al., "Treatment Results Using a Mixed Fiber Mesh in Patients With Grade IV Cystocele", Journal of Urology, vol. 161, Apr. 1999, pp. 1255-1258.
Moir et al., "The Gauze-Hammock Operation", The Journal of Obstetrics and Gynaecology of British Commonwealth, vol. 75, No. 1, Jan. 1968, pp. 1-9.
Morgan et al., "A Sling Operation, Using Madex Polypropylene Mesh, for the Treatment of Recurrent Stress Incontinence", Am J. Obst. & Gynecol, Feb. 1970, pp. 369-377.
Morgan, J.E., "The Marlex Sling Operation for the Treatment of Recurrent Stress Urinary Incontinence: A 16-year Review", American Obstetrics Gynecology, vol. 151, No. 2, Jan. 1998, pp. 224-226.
Morley et al., "Sacrospinous Ligament Fixations for Eversion of the Vagina", Am J Obstet Gyn, vol. 158, No. 4, Apr. 1988, pp. 872-881.
Mouly et al., "Vaginal Reconstruction of a Complete Vaginal Prolapse: The Trans Obturator Repair", Journal of Urology, vol. 169, Apr. 2003, pp. 183.
Narik et al., "A Simplified Sling Operation Suitable for Routine Use", Gynecological and Obstetrical Clinic, University of Vienna, vol. 84, No. 3, Aug. 1, 1962, pp. 400-405.
Natale et al., "Tension Free Cystocele Repair (TCR): Long-term Follow-up", International Urogynecology Journal, vol. 11, Supp. 1, Oct. 2000, pp. S51.
Nichols, David H., "The Mersilene Mesh Gauze-hammock for Severe Urinary Stress Incontinence", Obstetrics and Gynecology, vol. 41, Jan. 1973, pp. 88-93.
Nicita, Giulio, "A New Operation for Genitourinary Prolapse", Journal of Urology, vol. 160, Sep. 1998, pp. 741-745.

(56) References Cited

OTHER PUBLICATIONS

Niknejad et al., "Autologous and Synthetic Urethral Slings for Female Incontinence", Urol Clin N Am, vol. 29, 2002, pp. 597-611.
Morris et al., "Use of Synthetic Material in Sling Surgery: A Minimally Invasive Approach", Journal of Endourology, vol. 10, Issue 3, Jun. 1996, pp. 227-230.
O'Donnell, Pat, "Combined Raz Urethral Suspension and Mcguire Pubovaginal Sling for Treatment of Complicated Stress Urinary Incontinence", Journal Arkansas Medical Society, vol. 88, Jan. 1992, pp. 389-392.
Ostergard et al., "Urogynecology and Urodynamics Theory and Practice", 1996, pp. 569-579.
Paraiso et al., "Laparoscopic Surgery for Enterocele, Vaginal Apex Prolapse and Rectocele", Int. Urogx:necol J, vol. 10, 1999, pp. 223-229.
Parra et al., "Experience with a Simplified Technique for the Treatment of Female Stress Urinary Incontinence", British Journal of Urology, vol. 66, Issue 6, Dec. 1990, pp. 615-617.
Pelosi et al., "Pubic Bone Suburethral Stabilization Sling: Laparoscopic Assessment of a Transvaginal Operation for the Treatment of Stress Urinary Incontinence", Journal of Laparoendoscopic & Advaned Surgical Techniques, vol. 9, No. 1, Feb. 1999, pp. 45-50.
Pereyra, "A Simplified Surgical Procedure for the Correction of Stress Incontinence in Women", West. J. Surg. Obstetrics and Gynecology, 1959, pp. 223-226.
Pereyra et al., "Pubourethral Supports in Perspective: Modified Pereyra Procedure for Urinary Incontinence", Obstetrics and Gynecology, vol. 59, No. 5, May 1982, pp. 643-648.
Petros et al., "An Analysis of Rapid Pad Testing and the History for the Diagnosis of Stress Incontinence", Acta Obstet Gynecol Scand, vol. 71, 1992, pp. 529-536.
Petros et al., "An Integral Theory and Its Method for the Diagnosis and Management of Female Urinary Incontinence", Scandinavian Journal of Urology and Nephrology, Supp. 153, 1993, 1 page.
Petros et al., "Anchoring the Midurethra Restores Bladder-neck Anatomy and Continence", The Lancet, vol. 354, Sep. 18, 1999, pp. 997-998.
Petros, Peter E., "Cough Transmission Ratio: An Indicator of Suburethral Vaginal Wall Tension Rather Than Urethral Closure", Acta Obstet Gynecol Scand, vol. 69, Sup 153, 1990, pp. 37-39.
Petros et al., "Cure of Stress Incontinence by Repair of External Anal Sphincter", Acta Obstet Gvnecol Scand, vol. 69, Supp 153, 1990, 75 pages.
Petros, Peter, "Cure of Urge Incontinence by the Combined Intravaginal Sling and Tuck Operation", Acta Obstet Gynecol Scand, vol. 69, Sup 153, 1990, pp. 61-62.
Petros, Peter, "Development of Generic Models for Ambulatory Vaginal Surgery Preliminary Report", International Urogynecology Journal, 1998, pp. 20-27.
Petros et al., "Further Development of the Intravaginal Slingplasty Procedure—IVS III—(With Midline "Tuck")", Scandinavian Journal of Neurourology and Urodynamics, Supp. 153, 1993, pp. 69-71.
Petros et al., "Integral Therory of Female Urinary Incontinence", Acta Obstetricia et Gynecologica Scandinavica, vol. 69, Sup 153, 1990, pp. 7-31.
Petros et al., "Medium-term Follow-up of the Intravaginal Slingplasty Operation Indicates Minimal Deterioration of Urinary Continence With Time", 1999, 3 pages.
Petros, "New Ambulatory Surgical Methods Using an Anatomical Classification of Urinary Dysfunction Improve Stress Urge and Abnormal Emptying", Int. Urogynecology Journal Pelvic Floor Dystfunction, vol. 8, 1997, pp. 270-278.
Petros, Peter, "Part 1: Theoretical, Morphological, Radiographical Correlations and Clinical Perspective", Scandinavian Journal of Neurourology and Urodynamics Sup. 153, 1993, pp. 5-28.
Petros et al., "Part II: The Biomechanics of Vaginal Tissue and Supporting Ligaments With Special Relevance to the Pathogenesis of Female Urinary Incontinence", Scandinavian Journal of Neurourology and Urodynamics Sup. 153, 1993, pp. 29-40 (Plus CoverSheet).
Petros et al., "Part III: Surgical Principles Deriving From the Theory", Scandinavian Journal of Neurourology and Urodynamics, Sup. 153, 1993, pp. 41-52.
Petros et al., "Part IV: Surgical Appliations of the Theory Development of the Intravaginal Sling Pklasty (IVS) Procedure", Scandinavian Journal of Neurourology and Urodynamics, Sup 153, 1993, pp. 53-54.
Petros et al., "Pinch Test for Diagnosis of Stress Urinary Incontinence", Acta Obstet Gynecol Scand, vol. 69, Sup. 153, 1990, pp. 33-35.
Petros et al., "Pregnancy Effects on the Intravaginal Sling Operation", Acta Obstet Gynecol Scand, vol. 69, Sup. 153, 1990, pp. 77-79.
Petros et al., "The Autogenic Ligament Procedure: A Technique for Planned Formation of an Artificial Neo-ligament", Acta Obstet Gynecol Scand,vol. 69, Sup 153, 1990, pp. 43-51.
Petros et al., "The Combined Intravaginal Sling and Tuck Operation an Ambulatory Procedure for Cure of Stress and Urge Incontinence", Acta Obstet Gynecol Scand, vol. 69,Sup 153, 1990, pp. 53-59.
Petros et al., "The Development of the Intravaginal Slingplasty Procedure: IVS II—(With Bilateral "Tucks")", Scandinavian Journal of Neurourology and Urodynamics, Sup 153, 1993, pp. 61-67.
Petros et al., "The Free Graft Procedure for Cure of the Tethered Vagina Syndrome", Scandinavian Journal of Neurourology and Urodynamics, Sup 153, 1993, pp. 85-87.
Petros et al., "The Further Development of the Intravaginal Slingplasty Procedure—IVS V—(With "Double Breasted" Unattached Vaginal Flap Repair and Permanent Sling)", Scandinavian Journal of Neurourology and Urodynamics, Sup 153, 1993, pp. 73-75.
Petros et al., "The Further Development of the Intravaginal Slingplasty Procedure—IVS V—(With "Double Breasted" Unattached Vaginal Flap Repair and Permanent Sling)", Scandinavian Journal of Neurourology and Urodynamics,Sup 153, 1993, pp. 77-79.
Petros, Peter, "The Intravaginal Slingplasty Operation, a Minimally Invasive Technique for Cure of Urinary Incontinence in the Female", Australian and New Zealand Journal of Obstetrics and Gynaecology vol. 36, Issue 4, Nov. 1996, pp. 453-461.
Petros et al., "The Intravaginal Slingplasty Procedure: IVS VI—Further Development of the "Double Breasted", Vaginal Flap Repair-attached Flap", Scandinavian Journal of Neurourology and Urodynamics, Sup 153, 1993, pp. 81-84.
Petros et al., "The Posterior Fornix Syn6rome: A Multiple Symptom Complex of Pelvic Pain and Abnormal Urinary Symptoms Deriving From Laxity in the Posterior Fornix of Vagina", Scandinavian Journal of Neurourlogy and Urodynamics, Sup 153, 1993, pp. 89-93.
Petros et al., "The Role of a Lax Posterior Vaginal Fomix in the Causation of Stress and Urgency Symptoms: A Preliminary Report", Acta Obstet Gynecol Scand,vol. 69,Sup 153, 1990, pp. 71-73.
Petros et al., "The Tethered Vagina Syndrome Post Surgical Incontinence and I-Plasty Operation for Cure", Acta Obstet Gynecol Scand,vol. 69 Sup 153, 1990, pp. 63-67.
Petros et al., "The Tuck Procedure: A Simplified Vaginal Repair for Treatment of Female Urinary Incontinence", Acta Obstet Gynecol Scand,vol. 69 Sup 153, 1990, pp. 41-42.
Petros et al., "Urethral Pressure Increase on Effort Originates from Within the Urethra, and Continence From Musculovaginal Closure", Neurourology and Urodynamics vol. 14 No. 4, 1995, pp. 337-346.
Petros, Peter, "Vault Prolapse II: Restoration of Dynamic Vaginal Supports by Infracoccygeal Sacropexy an Axial Day-case Vaginal Procedure", Int Urogynecol J vol. 12, 2001, pp. 296-303.
Petros et al., "An Anatomical Basis for Success and Failure of Female Incontinence Surgery", Scandinavian Journal of Neurourology and Urodynamics, Sup 153, 1993, pp. 55-60.
Petros et al., "Bladder Instability in Women: A Premature Activation of the Micturition Reflex", Scandinavian Journal of Neurourology and Urodynamics, Sup 153, 1993, pp. 235-239.
Petros et al., "Non Stress Non Urge Female Urinary Incontinence—Diagnosis and Cure: A Preliminary Report", Acta Obstet Gynecol Scand, vol. 69, Sup 153, 1990, pp. 69-70.

(56) References Cited

OTHER PUBLICATIONS

Petros et al., "Pelvic Floor Rehabilitation According to the Integrated Theory of Female Urinary Incontinence", Chapter 7, pp. 249-258.
Pourdeyhimi, B, "Porosity of Surgical Mesh Fabrics: New Technology", J. Biomed. Mater. Res.: Applied Biomaterials, vol. 23, No. A1, 1989, pp. 145-152.
Rackley, Raymond, "Synthetic Slings: Five Steps for Successful Placement", Urology Times, 2000, pp. 46,48,49.
Rackley et al., "Tension-free Vaginal Tape and Percutaneous Vaginal Tape Sling Procedures", Techniques in Urology, vol. 7, No. 2, 2001, pp. 90-100.
Rackley, Raymond, "The Raz Bladder Neck Suspension Results in 206 Patients", The Journal of Urology, 1992, pp. 845-846.
Raz, Shlomo, "Female Urology", 1996, pp. 80-86, 369-398 & 435-442.
Raz, Shlomo, "Modified Bladder Neck Suspension for Female Stress Incontinence", Urology vol. 17, No. 1, Jan. 1981, pp. 82-85.
Richardson et al., "Delayed Reaction to the Dacron Buttress Used In Urethropexy", The Journal of Reproductive Medicine, vol. 29, No. 9, 1984, pp. 689-692.
Richter, K, "Massive Eversion of the Vagina: Pathogenesis Diagnosis and Therapy of the "True" Prolapse of the Vaginal Stump", Clin Obstet Gynecol, vol. 25, 1982, pp. 897-912.
Ridley, John, "Appraisal of the Goebell-Frangenheim-Stoeckel Sling Procedure", American Journal Obst & Gynec, vol. 95,No. 5, Jul. 1, 1986, pp. 741-721.
Roberts, Henry, "Cystourethrography in Women", Department of Obstetrics and Gynaecology, University of Liverpool, vol. XXXV, No. 293, 1952, pp. 253-259.
Sanz et al., "Modification of Abdominal Sacrocolpopexy Using a Suture Anchor System", The Journal of Reproductive Medicine, vol. 48, No. 7, Jul. 2003, pp. 496-500.
Seim et al., "A Study of Female Urinary Incontinence in General Practice", Demography, Medical History, and Clinical Findings,Scandinavian Journal of Urology and Nephrology,vol. 30, 1996, pp. 465-472.
Sergent et al., "Prosthetic Restoration of the Pelvic Diaphragm in Genital Urinary Prolapse Surgery: Transobturator and Infacoccygeal Hammock Technique", J Gynecol Obstet Biol Reprod, vol. 32, 2003, pp. 120-126.
Sloan et al., "Stress Incontinence of Urine: A Retrospective Study of the Complications and Late Results of Simple Suprapubic Suburethral Fascial Slings", The Journal of Urology,vol. 110, 1973, pp. 533-536.
Spencer et al., "A Comparison of Endoscopic Suspension of the Vesical Neck With Suprapubic Vesicourethropexy for Treatment of Stress Urinary Incontinence", The Journal of Urology, vol. 137, 1987, pp. 411-415.
Stamey, Thomas A., "Endoscopic Suspension of the Vesical Neck for Urinary Incontinence in Females", Annals of Surgery vol. 192 No. 4, Oct. 1980, pp. 465-471.
Stanton, Stuart L., "Suprapubic Approaches for Stress Incontinence in Women", Journal of American Geriatrics Society,vol. 38,No. 3, 1990, pp. 348-351.
Stanton et al., "Surgery of Female Incontinence", 1986, pp. 105-113.
Staskin et al., "A Comparison of Tensile Strength among Three Preparations of Irradiated and Non-Irradiated Human Fascia Lata Allografts", 2 pages.
Staskin et al., "The Gore-tex sling procedure for female sphincteric incontinence: indications, technique, and results", World J of Urol. vol. 15 No. 5, 1997, pp. 295-299.
Studdiford, William E., "Transplantation of Abdominal Fascia for the Relief of Urinary Stress Incontinence", American Journal of Obstetrics and Gynecology, 1944, pp. 764-775.
Subak et al., "Cost of Pelvic Organ Prolapse Surgery in the United States", Obstetrics & Gynecology, vol. 98, No. 4, Oct. 2001, pp. 857-863.
Sullivan et al., "Total Pelvic Mesh Repair a Ten-Year Experience", Dis. Colon Rectum, vol. 44, No. 6, Jun. 2001, pp. 857-863.
SUPORT™, "Sub-Urethral Perineal Retro-Pubic Tensionless Sling", Matrix Medical (Pvt) Ltd, 1 page.
Swift, S. E., "Case-Control Study of Etiologic Factors in the Development of Sever Pelvic Organ Prolapse", Int Urogynecol J, vol. 12, 2001, pp. 187-192.
T-SLING®, "Urinary Incontinence Procedure", (Totally Tension-free) Hemiamesh, 2 pages.
TVT, "Tension-free Vaginal Tape", Gynecare, Ethicon, Inc., 1999, 23 pages.
Ulmsten et al., "A Multicenter Study of Tension-free Vaginal Tape (TVT) for Surgical Treatment of Stress Urinary Incontinence", International Urogynecology Journal, vol. 9, 1998, pp. 210-213.
Ulmsten et al., "A Three Year Follow up of Tension Free Vaginal Tape for Surgical Treatment of Female Stress Urinary Incontinence", British Journal of Obstetrics and Gynaecology, vol. 106, 1999, pp. 345-350.
Ulmsten et al., "An Ambulatory Surgical Procedure Under Local Anesthesia for Treatment of Female Urinary Incontinence", International Urogynecology Journal, vol. 7, May 1996, pp. 81-86.
Ulmsten et al., "Different Biochemical Composition of Connective Tissue in Continent", Acta Obstet Gynecol Scand, 1987, pp. 455-457.
Ulmsten et al., "Intravaginal Slingplasty (IVS): An Ambulatory Surgical Procedure for Treatment of Female Urinary Incontinence", Scand J Urol Nephrol, vol. 29, 1995, pp. 75-82.
Ulmsten et al., "The Unstable Female Urethra", Am. J. Obstet. Gynecol., vol. 144 No. 1, Sep. 1, 1982, pp. 93-97.
Ulmsten, U., "Female Urinary Incontinence—A Symptom, Not a Urodynamic Disease. Some Theoretical and Practical Aspects on the Diagnosis a Treatment of Female Urinary Incontinence", International Urogynecology Journal, vol. 6, 1995, pp. 2-3.
VESICA®, "Percutaneous Bladder Neck Stabilization Kit", A New Approach to Bladder Neck Suspenison, Microvasive® Boston Scientific Corporation, 1995, 4 pages.
VESICA®, "Sling Kits", Simplifying Sling Procedures, Microvasive® Boston Scientific Corporation, 1998, 4 pages.
Villet et al., "Gynecolgie Obstetrique & Fertile", vol. 31, 2003, p. 96.
Visco et al., "Vaginal Mesh Erosion After Abdominal Sacral Colpopexy", Am J Obstet Gynecol, vol. 184, n. 3, pp. 297-302.
Walters, Mark D., "Percutaneous Suburethral Slings: State of the Art", Presented at the conference of the American Urogynecologic Society, Chicago, Oct. 2001, 29 pages.
Waxman et al., "Advanced Urologic Surgery for Urinary Incontinence", The Female Patient, vol. 21, Mar. 1996, pp. 93-100.
Weber et al., "Anterior Vaginal Prolapse: Review of Anatomy and Techniques of Surgical Repair", Obstetrics and Gynecology, vol. 89, No. 2, Feb. 1997, pp. 311-318.
Webster, George D., "Female Urinary Incontinence", Urologic Surgery, pp. 665-679.
Webster et al., "Voiding Dysfunction Following Cystourethropexy: Its Evaluation and Management", The Journal of Urology, vol. 144, Sep. 1990, pp. 670-673.
Winter, Chester C., "Peripubic Urethropexy for Urinary Stress Incontinence in Women", Urology, vol. XX, No. 4, Oct. 1982, pp. 408-411.
Winters et al., "Abdominal Sacral Colpopexy and Abdominal Enterocele Repair in the Management of Vaginal Vault Prolapse", Urology, vol. 56, supp. 6A, 2000, pp. 55-63.
Woodside et al., "Suprapubic Endoscopic Vesical Neck Suspension for the Management of Urinary Incontinence in Myelodysplastic Girls", The Journal of Urology, vol. 135, Jan. 1986, pp. 97-99.
Zacharin et al., "Pulsion Enterocele: Long-term Results of an Abdominoperineal Technique", Obstetrics & Gynecology, vol. 55 No. 2, Feb. 1980, pp. 141-148.
Zacharin, Robert, "The Suspensory Mechanism of the Female Urethra", Journal of Anatomy, vol. 97, Part 3, 1963, pp. 423-427.
Zimmern et al., "Four-Comer Bladder Neck Suspension", Vaginal Surgery for the Urologist, vol. 2, No. 1, Apr. 1994, pp. 29-36.
U.S. Appl. No. 15/618,102, filed Jun. 8, 2017.
U.S. Appl. No. 13/060,467, filed May 4, 2011.

(56) References Cited

OTHER PUBLICATIONS

U.S. Appl. No. 13/335,472, filed Dec. 22, 2011.
U.S. Appl. No. 14/697,525, filed Apr. 27, 2015.

* cited by examiner

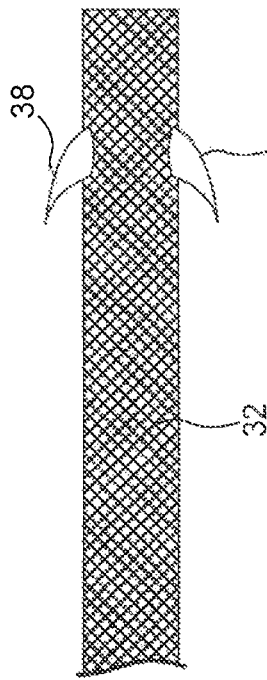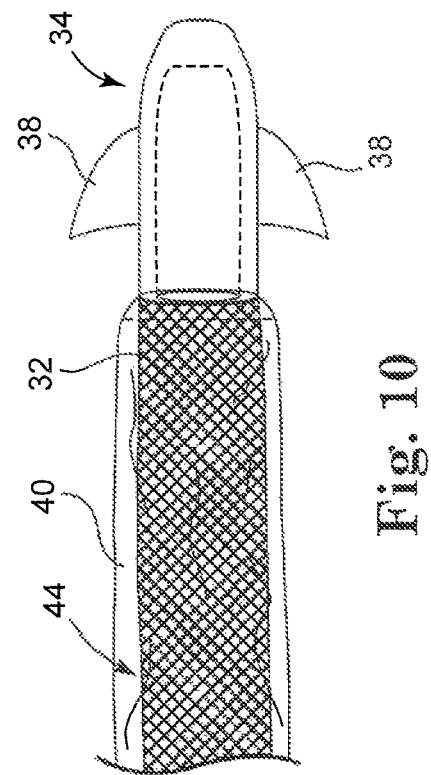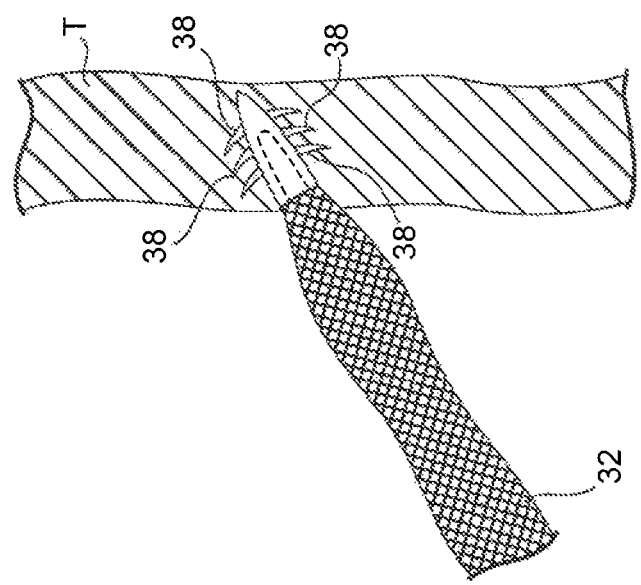

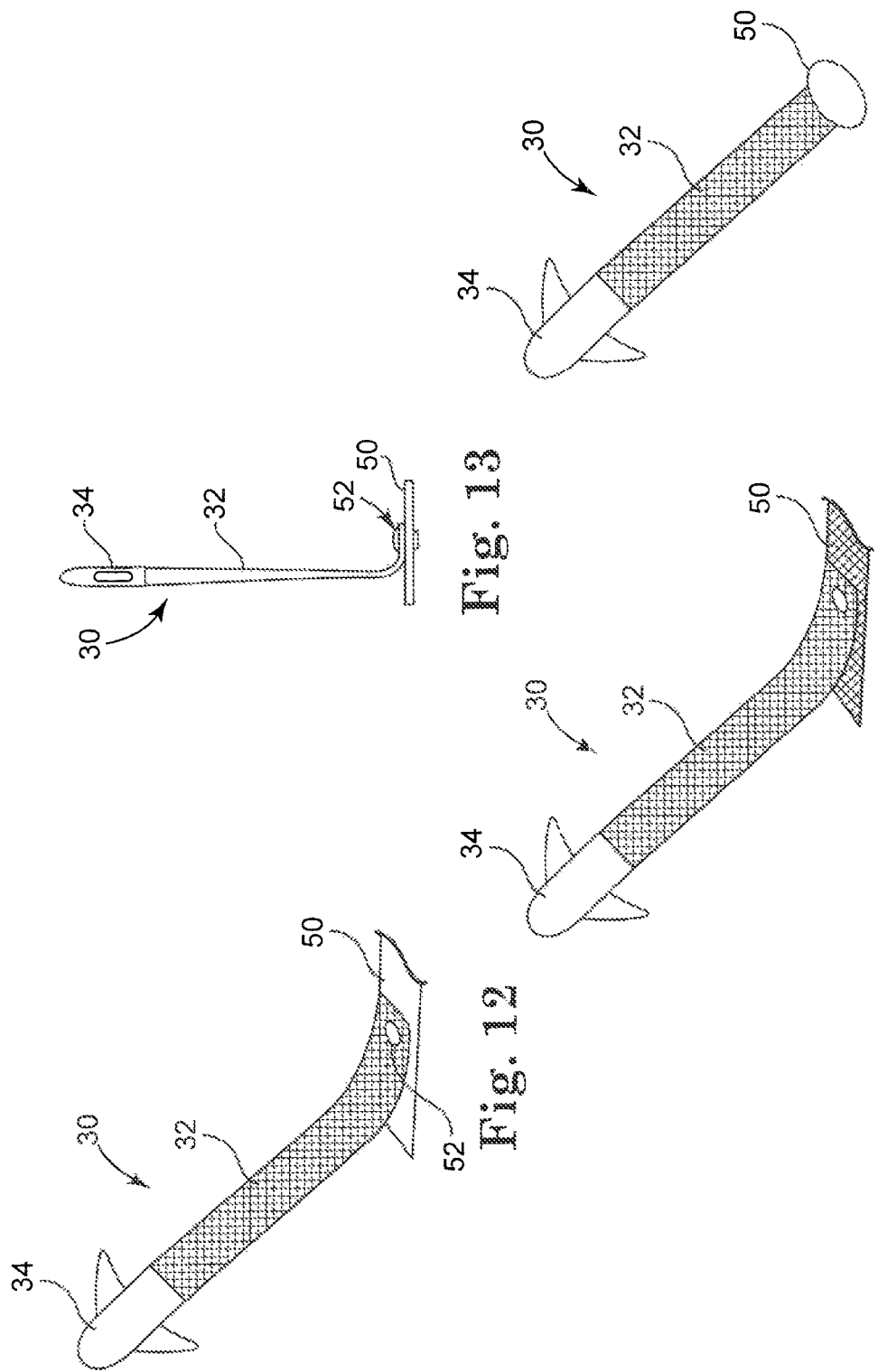

MINIMALLY INVASIVE IMPLANT AND METHOD

CROSS-REFERENCE TO RELATED APPLICATIONS

This application is a Continuation of, and claims priority to, U.S. patent application Ser. No. 15/618,102, filed on Jun. 8, 2017, which is a Continuation of U.S. patent application Ser. No. 14/697,525, filed on Apr. 27, 2015, now U.S. Pat. No. 9,867,685, which is a Divisional of U.S. application Ser. No. 13/335,472, filed on Dec. 22, 2011, now U.S. Pat. No. 9,017,243, which is a Continuation-In-Part of U.S. application Ser. No. 13/060,467, filed on May 4, 2011, now U.S. Pat. No. 8,968,181, and which claims priority to and the benefit of U.S. Provisional Application No. 61/426,117, filed on Dec. 22, 2010, and U.S. application Ser. No. 13/060,467 claims priority to and the benefit of International PCT Patent Application No. PCT/US2009/054909, filed on Aug. 25, 2009, which claims priority to and the benefit of U.S. Provisional Application No. 61/091,586, filed on Aug. 25, 2008; with each of the above-referenced applications being fully incorporated herein by reference in their entirety.

FIELD OF THE INVENTION

The present invention relates to apparatus, tools and methods for treating pelvic conditions by providing and using one or more pelvic implants to support pelvic tissue.

BACKGROUND OF THE INVENTION

It has been reported that over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. FIG. 1 schematically illustrates the relevant female anatomy. The urethra 16 is the tube that passes urine from the bladder 14 out of the body. The narrow, internal opening of the urethra 16 within the bladder 14 is the bladder neck 18. In this region, the bladder's bundled muscular fibers transition into a sphincteric striated muscle called the internal sphincter. FIG. 2 schematically illustrates the relevant male anatomy. The urethra 16 extends from the bladder neck 18 to the end of the penis 22. The male urethra 16 is composed of three portions: the prostatic, bulbar and pendulus portions. The prostatic portion is the widest part of the tube, which passes through the prostate gland 24. FIG. 3 is a schematic view of the anatomy of the anus and rectum. The rectum 1 is the most distal portion of the gastrointestinal tract. The exterior opening of the rectum is the anus 2. Fecal continence is related to control of the exterior sphincter 3 and interior sphincter 4 of the anus.

Urinary incontinence may occur when the muscles of the urinary system are injured, malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intraabdominal pressure resulting from activities such as coughing, sneezing, lifting, straining, exercise and, in severe cases, even simply changing body position. Urge incontinence, also termed "hyperactive bladder" "frequency/urgency syndrome" or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

SUI is generally thought to be related to hypermobility of the bladder neck or an intrinsic urethral sphincter defect. A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of SUI can include lifestyle changes, such as weight loss, smoking cessation, and modification of intake of diuretic fluids such as coffee and alcohol. With regard to surgical treatments, the purported "gold standard" is the Burch Colposuspension in which the bladder neck is suspended. Mid-urethral slings have been similarly effective. One type of procedure, found to be an especially successful treatment option for SUI in both men and women, is a sling and support procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension structures or sutures to a point of attachment (e.g., tissue or bone) through an abdominal and/or vaginal incision.

Although serious complications associated with sling procedures are infrequent, they can occur. Complications for certain sling procedures may include urethral obstruction, development of de nova urge incontinence, hemorrhage, prolonged urinary retention, infection, damage to surrounding tissue and erosion.

Fecal incontinence, like urinary incontinence, has proven to be challenging to treat. Patients whose fecal incontinence is caused by external anal sphincter injury is treated surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic gracilloplasty, artificial sphincter procedures, and sacral nerve stimulation. Success has been limited, and the various treatment modalities can result in morbidity.

There is a desire for a minimally invasive yet highly effective treatment modality that can be used with minimal to no side effects for the treatment of both urinary and fecal incontinence. Further, the method of treatment should also improve the quality of life for patients.

SUMMARY OF THE INVENTION

The present invention can include surgical instruments, implantable articles, and methods for urological applications, particularly for the treatment of stress and/or urge urinary incontinence, fecal incontinence, and prolapse and perinea! floor repairs. As noted, the usual treatments for SUI include placing a sling to either compress the urethral sphincter or to elevate or support the neck of the bladder defects.

Embodiments of the present invention can include apparatus and methods for treating urinary incontinence, fecal incontinence, and other pelvic defects or dysfunctions, in both males and females using one or more lateral implants to reinforce the supportive tissue of the urethra. The implants are configured to engage and pull (e.g., pull up) lateral urethral support (e.g., endopelvic fascia) tissue to cause the sub-urethral tissue to tighten and provide slack reduction for improved support. As such, the implants of such embodiments can be utilized to eliminate the need for mesh or other supportive structures under the urethra that is common with other incontinence slings. The implants can be shaped to facilitate such support, e.g., provided with anchoring end portions or configurable in "U," "V" or like shapes. Further, one or more anchors or tissue engagement portions can be employed to attach and stabilize the implants to the tissue. Other embodiments of the present invention can include a supportive sling implant having one or more arm portions and a tensioning rod. Such embodiments can be provided in a traditional supportive configuration under the urethra, or laterally positioning with respect to the urethra, as described herein. In various such embodiments, the sling can include a tissue support portion having a first eyelet and a second eyelet, a first extension arm, and a second extension arm. The first extension arm can include an anchor portion and an opposing end adjustment element, with at least a length of the first extension arm adapted to slide through the first eyelet of the tissue support portion. Similarly, the second extension arm can include an anchor portion and an opposing end adjustment element, with at least a length of the first extension arm adapted to slide through the second eyelet of the tissue support portion.

The support portion can be included with one of the extension arms to provide a two-piece construct. For instance, the first extension arm and its corresponding support portion can include the eyelet and an anchoring portion. The second arm extension can slidably engage with the eyelet to define the elongate sling. Alternatively, the support portion can be a separate element of a three-piece construct. As such, the support portion for such embodiments can include two or more eyelets. Two separate extension arms can be included with such embodiments (e.g., each with anchors and adjustment elements), with each extension arm adapted to slidably engage with a respective eyelet of the separate support portion.

Certain embodiments of the implant or sling can include one or more indicia to assist in deployment, adjustment and tensioning of the implant or sling.

Embodiments of the present invention can provide smaller implants, fewer implant components, thus reducing the size and number of incisions, improving implant manipulation and adjustment, and the complexity of the insertion and deployment steps.

BRIEF DESCRIPTION OF THE DRAWINGS

FIG. 9 shows a pelvic implant device having anchoring members along a portion of the extension portion in accordance with embodiments of the present invention.

FIG. 10 shows an anchoring pelvic implant device in accordance with embodiments of the present invention.

FIG. 11 shows a pelvic implant device having a multi-barbed anchor in accordance with embodiments of the present invention.

FIGS. 12-15 show various pelvic implant devices with a leading anchor and a trailing base or bulk anchor in accordance with embodiments of the present invention.

DETAILED DESCRIPTION OF PREFERRED EMBODIMENTS

Figure 1:
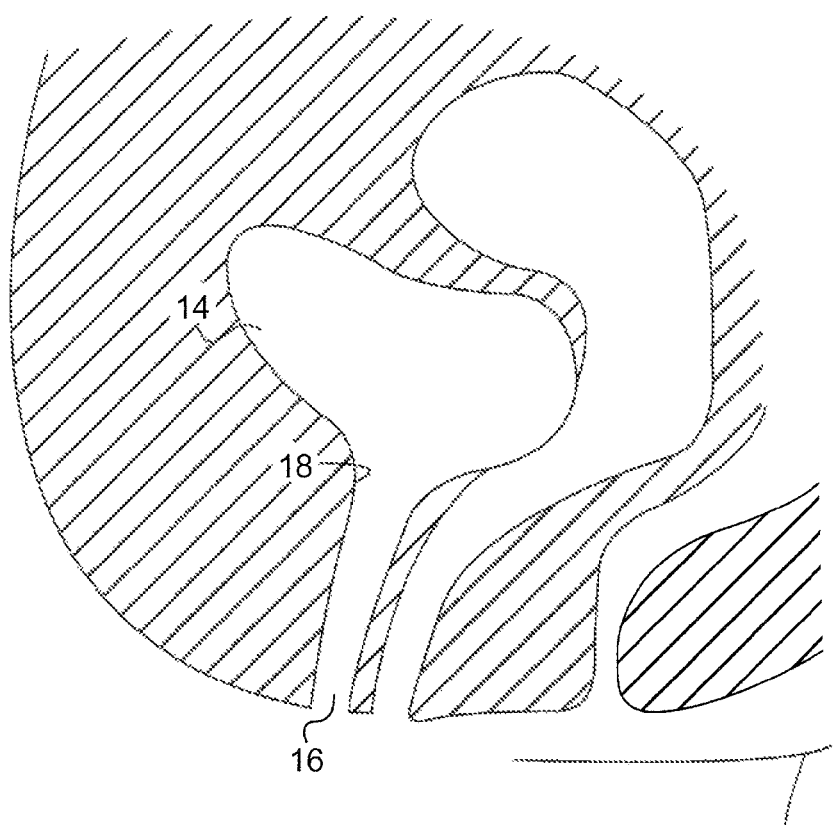
FIG. 1 shows a schematic view of the female urinary system.
Figure 2:
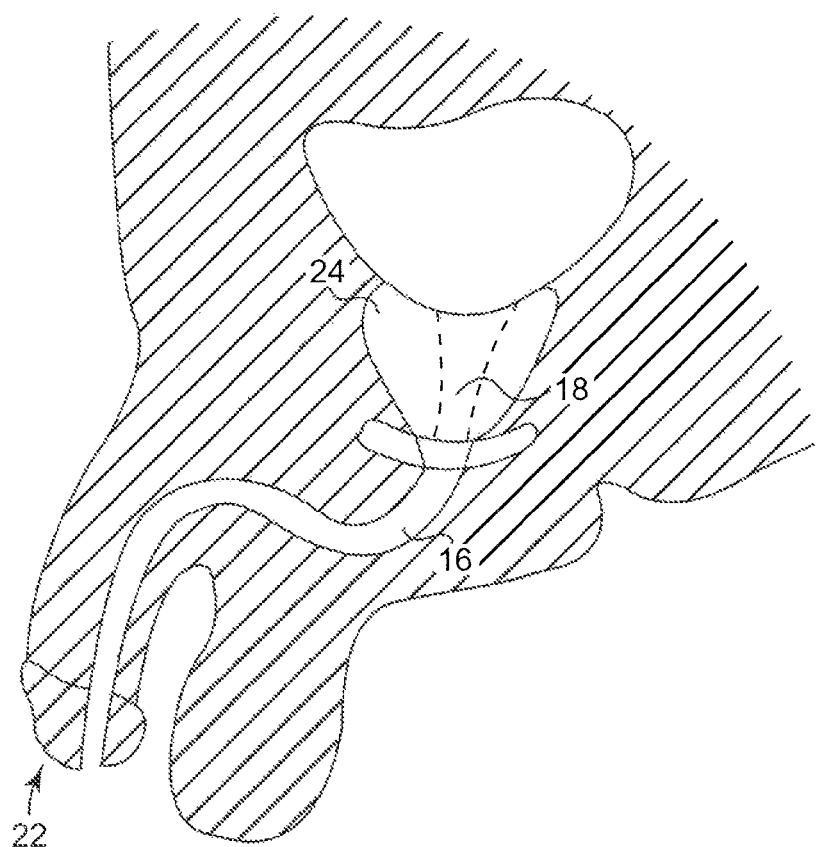
FIG. 2 shows a schematic view of the male urinary system.
Figure 3:
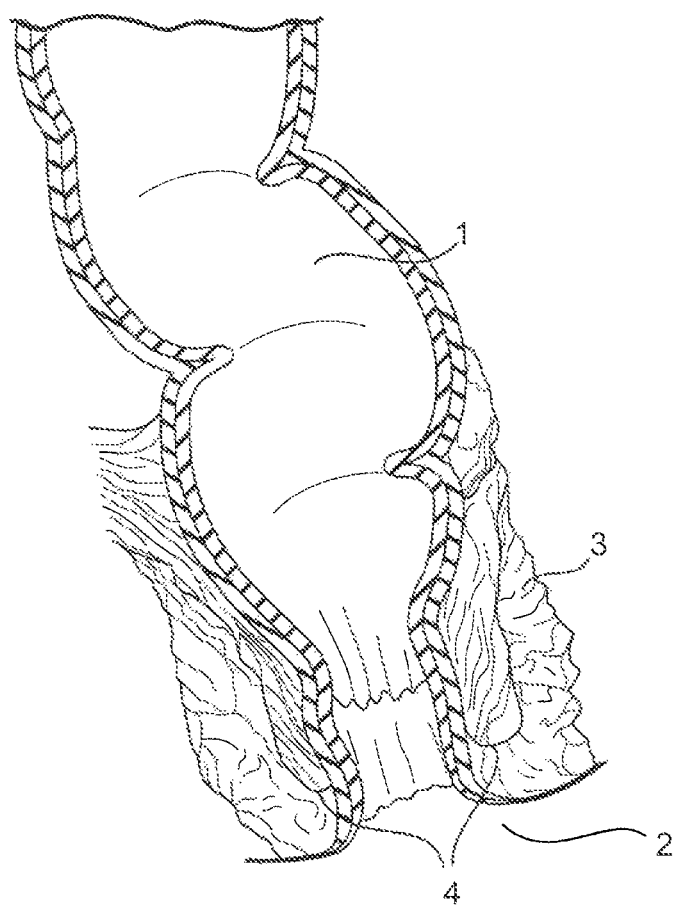
FIG. 3 shows a schematic view of the anatomy of the anus and rectum.

Referring generally to FIGS. 1-41, like reference numerals can designate identical, similar or corresponding parts throughout the views. The following description is meant to be illustrative only, and not limiting other embodiments of this invention that will be apparent to those of ordinary skill in the art in view of this description. One aspect of the present invention is an apparatus and method of treating urinary incontinence in males or females. In various embodiments, one or more implants or implant members are placed in strategically located positions to pull up or otherwise tighten tissue and/or muscle lateral to the urethra to generally re-establish the original anatomical structure of the patient. Various systems, devices, structures, techniques and methods, alone or in combination, as disclosed in U.S. Pat. Nos. 6,911,003, 6,612,977, 6,802,807, 2002/0161382, 2004/0039453 and 2008/0045782, and International PCT Publication No. 2008/057261, can be employed with the present invention, with the above-identified disclosures being incorporated herein by reference in their entirety. The devices or structures described herein can be employed or introduced into the pelvic region of the patient transvaginally, percutaneously or in any other manner known by those of ordinary skill in the art.

Figure 4:
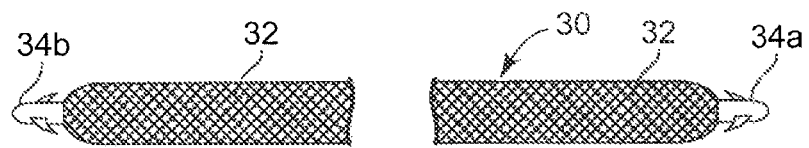
FIG. 4 shows a pelvic implant device in accordance with embodiments of the present invention.
Figure 5:
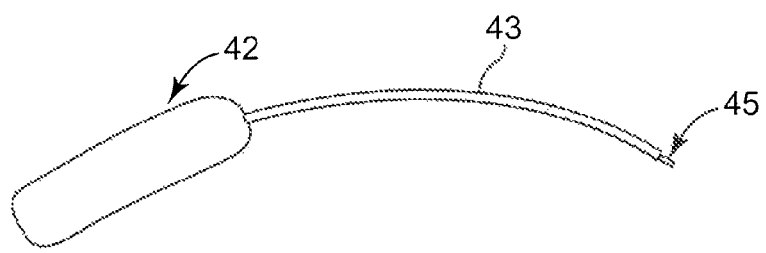
FIG. 5 shows an introducer or insertion device capable of use with embodiments of the present invention.

Various embodiments of the present invention can include a tensioning or support implant device 30 having an extension portion 32 and one or more engagement portions 34, as shown in FIG. 4. The one or more engagement portions can include a first anchor 34a at a first or leading end of the tensioning device 30, with a second anchor 34b provided at an opposite trailing end of the device 30. The extension portion 32 can be constructed of a compatible mesh or like porous material known for use and compatibility with urethral slings, other pelvic support devices, and the like. The mesh material can facilitate the infiltration of tissue and cells within the extension portion 32 to promote tissue in-growth and, in turn, fixation of the device 30 to the surrounding anatomical structure. The extension portion 32 can also include protrusions, serrated edges, extending fibers, or similar structural features to promote tissue fixation and ingrowth. In other embodiments, the extension portion 32 can be constructed of a flexible, or semi-rigid, length of a compatible generally non-porous material. The length and flexibility of the device 30 and corresponding extension portion 32 can vary greatly depending on the particular procedure and anatomical support application. The extension portion 32 can be generally planar at introduction, pre-shaped or pre-formed, or otherwise configured to allow for adaptation, manipulation and shaping during the implantation procedure. Various embodiments of the extension portion 32 can be capable of forming into a generally V-shaped or U-shaped device (FIG. 6), or otherwise adapted for flexible or selective manipulation and traversal through, around and/or along various tissue and muscles of the pelvic region. In certain embodiments, the length of the device 30 can range from 0.5 to 6 cm. It is also possible to have lengths greater than or less than 0.5 to 6 cm.

In certain embodiments, the implant can be constructed in the form of a collapsible synthetic mesh patch, and can include an adhesive covering (e.g., fibron glue). Further, an umbrella-like feature can be included with wire splines or members extending from the patch. The umbrella-like feature can be connected with the patch via a connection structure, such as a ring, fastener, etc. A portion of the implant introducer (e.g., plunger and/or wire) can be configured to advance the patch and deploy and/or expand the umbrella-like feature to provide tissue engagement for the patch.

Figure 6:
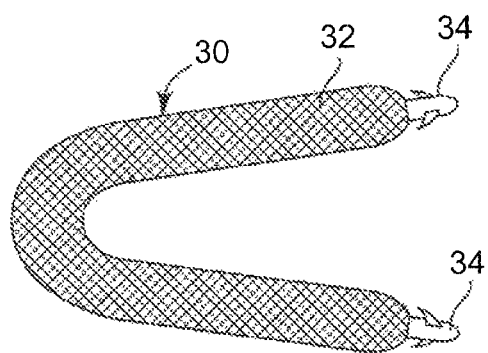
FIG. 6 shows a generally U-shaped pelvic implant device m accordance with embodiments of the present invention.
Figure 7:
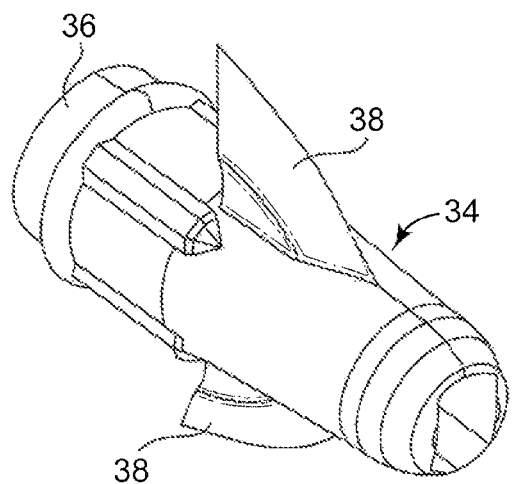
FIG. 7 shows an anchor of a pelvic implant device in accordance with embodiments of the present invention.
Figure 8:
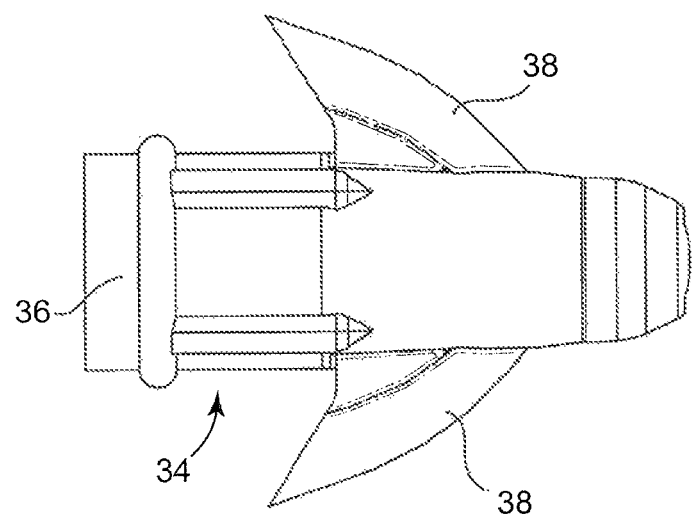
FIG. 8 shows a side view of the pelvic implant device anchor of FIG. 7.

The one or more engagement portions 34 can be configured as fixating, or self-fixating, tips or anchors 34 adapted for penetration and fixation within target tissue or muscle (T) of the pelvic region. As shown in FIGS. 4, 6 and 7-11, the anchors 34 can vary in shape, size and placement along the device 30. For instance, as shown in FIGS. 4 and 6, the anchors 34 can be integrated, attached or otherwise provided proximate the ends of the extension portion 32. The extension portion 32 can be connected to the anchors 34 via an end portion 36 of the anchors 34. A myriad of attachment structures or techniques can be utilized to connect the ends of the extension portion 32 to the end portion 36 of the anchors 34. Further, the anchors 34 can include opposing tines or barbs 38 to facilitate penetration and fixation within the target tissue. Other embodiments, such as those depicted in FIGS. 9-11, can include one or more tines 38 provided along portions of the extension portion 32 (FIG. 9), or a plurality of barbs 38 disposed along the anchors 34 (FIG. 11). Moreover, the one or more engagement portions 34 can be configured as toggle bolt anchors (FIG. 26), tubular members, planar members, bulbous members and the like, any of which can be constructed of compatible polymers, metals, mesh or non-porous materials, or bio-absorbable or non-absorbable materials. As depicted and described herein, the engagement portions 34 can be adapted to engage various target tissue regions, including the endopelvic fascia, the rectus fascia/muscle, the obturator muscle, and other anatomical structures of the pelvis.

In addition, a sheath or sleeve 40 can be selectively provided along a length of the extension portion 32 to facilitate introduction and insertion of the device 30 within the pelvic region of the patient, as depicted in FIG. 10. One or more insertion or introduction devices 42 can be employed to facilitate traversal of the device 30 within the pelvic region, and to facilitate deployment of the device 30 (e.g., anchors 34) into the target tissue location. Various known insertion devices 42 can be utilized, including those disclosed in the previously-incorporated patent references. A needle embodiment of the device 42 can include a handle, a tubular member 43 (straight or curved), and a tip 45 adapted for selective engagement with one or more components of the implants disclosed herein. As depicted in FIG. 10, the extension portion 32 can include a plurality of fibrous material or strands 44 adapted to further promote tissue ingrowth and fixation.

As detailed herein, various embodiments of the present invention are configured to treat urinary incontinence by providing support to the tissue or anatomical structure proximate or surrounding the urethra, rather than providing more conventional hammock-like support under the urethra. The device 30 and engagement aspects of the invention for such embodiments can vary greatly, as detailed herein.

As shown in FIGS. 12-15, the device 30 can include the barbed anchor 34 at a leading end of the extension portion 32 and a bulk base member 50 at the opposite trailing end. The extension portion 32 can be constructed of a mesh material (FIG. 12), or another porous or nonporous material (FIGS. 14-15). Further, the base member 50 can be mesh, or another porous or non-porous material, and can take on any variety of shapes, including planar, bulbous, tubular, etc. The base member 50 can be integrated with the extension portion 32, attached using fasteners 52 (e.g., rivet), bonded, or otherwise attached utilizing known structures and techniques. In other embodiments, the extension portion 32 can be made of random fibers, or a weaved, braided, twisted, or knitted polymer material.

Figure 16:
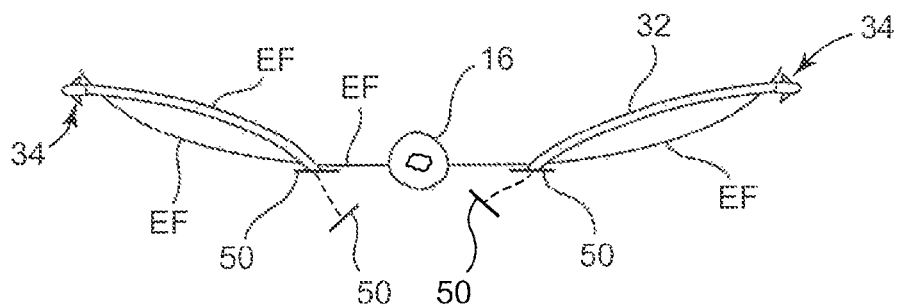
FIG. 16 shows the implantation of pelvic implant devices in the lateral urethral support tissue in accordance with embodiments of the present invention.

As depicted in FIG. 16, the device 30 can be inserted along a path generally toward the obturator foramen for penetration through the endopelvic fascia (EF) on either or both sides of the urethra 16. As such, the anchors 34 are positioned for fixation with tissue or muscle proximate the fascia so that the base member 50 is disposed on the entry side of the fascia. The base member 50 of each device 30 can be sized and shaped such that it remains on the entry side of the fascia and can include one or more anchors, protrusions or similar structures to provide additional engagement and retention against the fascia. The anchors 34 are advanced and positioned to penetrate through or otherwise engage with selective target tissue such that the laterally extending sub-urethral tissue, such as the endopelvic fascia, is pulled upward to remove slack and relocate the fascia and/or urethra to a more optimal and correct anatomical position. Other adjustment mechanisms and techniques can also be used to raise the fascia to provide the desired tightening or slack reduction in the laterally extending urethral support tissue. The devices 30 of FIGS. 14-15 function in the same manner, except that the extension portion 32 and base members 50 can assume different design configurations and can be constructed of different materials, such as relatively stiff or flexible polymers, mesh, non-porous mesh and other known compatible materials.

Structures or portions of the various embodiments detailed herein can be constructed of materials such as polypropylene, polyglycolide, poly-1-lactides, or other known biodegradable (re-absorbable) or non-biodegradable polymers. Further, growth factors or stem cells can be seeded or otherwise provided with one or more of the components of the device 30 to facilitate healing or tissue in-growth. In addition to introduction and deployment of the device 30 with a needle introducer device, a cannula or catheter system can be utilized as well.

Figure 17:
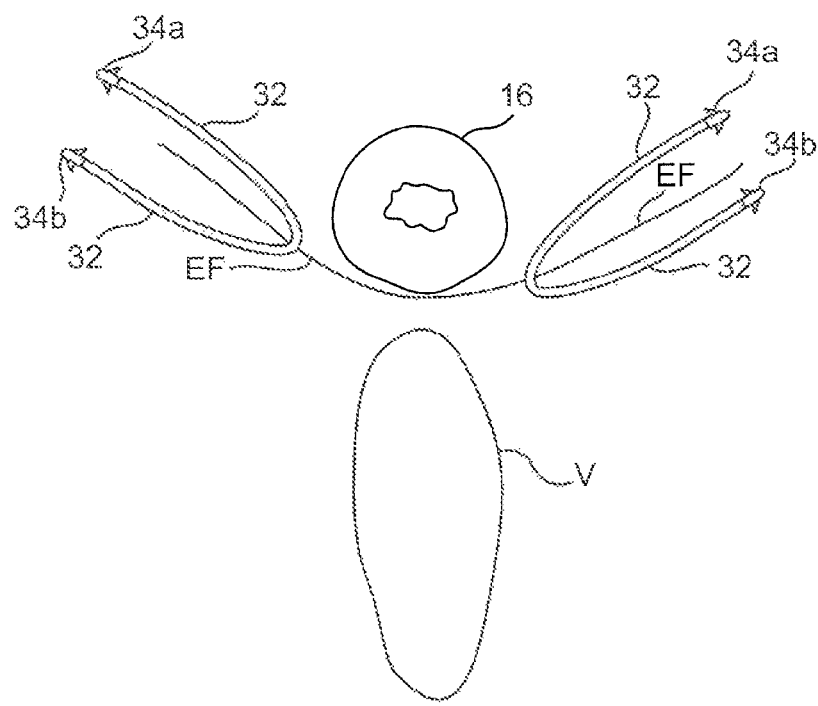
FIG. 17 schematically shows the implantation of U-shaped pelvic implant devices in the lateral urethral support tissue in accordance with embodiments of the present invention.

The embodiment of FIGS. 16-17 includes an implant device 30 having the extension portion 32 and one or more engagement or anchor portions 34 provided at an end region of the extension portion 32. The device 30 can be designed with a level of flexibility allowing a user to easily direct and advance the device 30 and to allow for manipulation of the device 30 into a generally U-shaped or similar configuration during deployment and anchoring. In one embodiment, the device 30 is adapted to generally augment the lateral tissue of the supportive pelvic floor of the patient. For instance, a first of the anchors 34a can be inserted through the endopelvic fascia for fixation within tissue. As such, the other anchor 34b can be adjusted or pulled to tighten and raise the supportive urethral tissue. One or more of the anchors 34a, 34b can be fixated to tissue near or at the obturator internus muscle or obturator membrane. Upon pulling the support tissue up to generally obtain the correct anatomical urethral support, the second anchor is fixated within the proximate tissue, with the bend of the extension portion 32 extending through the fascia. This process can be repeated for the supportive tissue on the other side of the urethra to provide bilateral augmentation and support.

Figure 18:
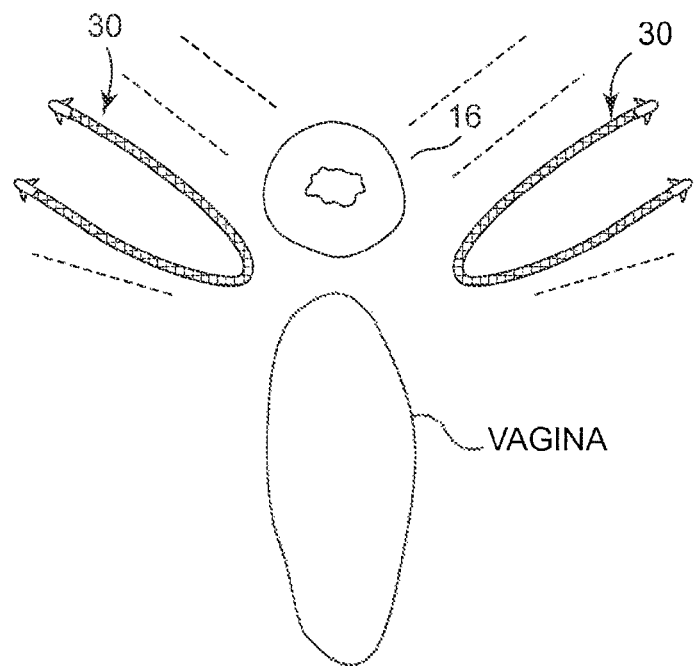
FIG. 18 schematically shows the implantation of U-shaped pelvic implant devices in the lateral urethral support tissue in accordance with embodiments of the present invention.
Figure 19:
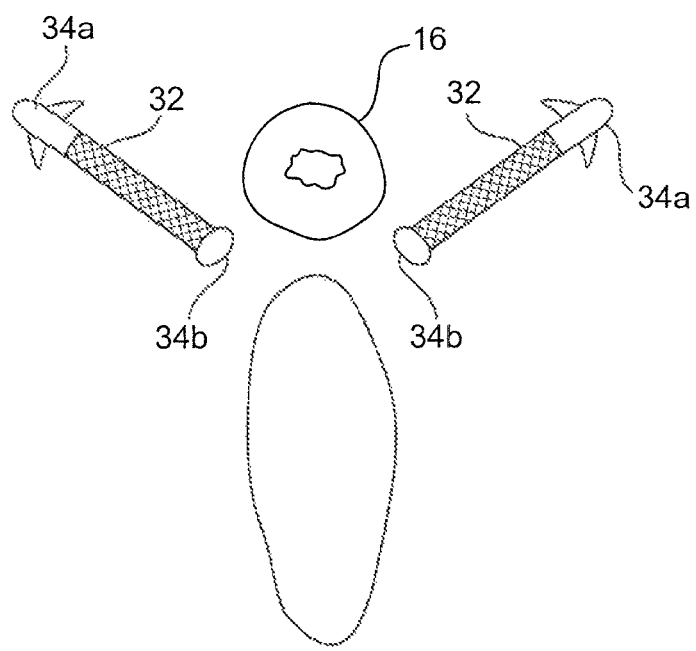
FIG. 19 schematically shows the implantation of implant devices, having leading anchor and trailing bulk anchors, to provide tensioning support for the lateral urethral support tissue in accordance with embodiments of the present invention.

FIG. 18 shows an embodiment of the device 30 having a first anchor 34a and a second anchor 34b, with the portion 32 extending therebetween. The anchors 34a, 34b can be configured in accordance with the various designs disclosed herein. For example, the first anchor 34a can be a penetrating tip, with the second anchor 34a be shaped as a tubular or bulk anchor. One of the anchors can be fixated in tissue above the fascia and the other of the anchors secured at, near or through the fascia to pull the supportive urethral tissue up to eliminate slack in the tissue. This process can be repeated on the other side of the urethra to provide bilateral augmentation and support. Embodiments of the extension portion 32 can be constructed of mesh, or braided, twisted, knitted, tubular, or collagen matrix materials to facilitate fixation and tissue in-growth. Further, a plurality of such devices 30 can be implanted on either or both sides of the urethra to promote tissue augmentation and support.

Figure 20:
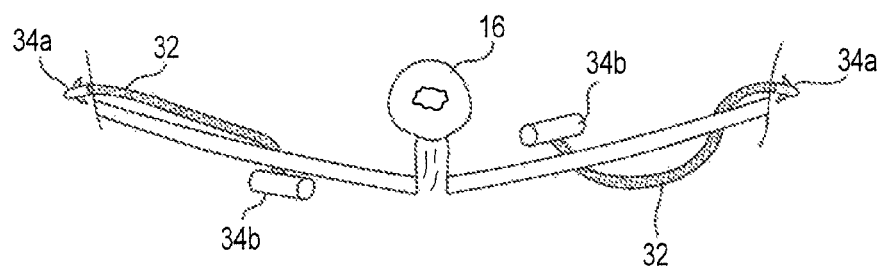
FIGS. 20-21 schematically show the implantation of implant devices, having leading anchor and trailing bulk anchors, to provide tensioning support for the lateral urethral support tissue in accordance with embodiments of the present invention.
Figure 21:
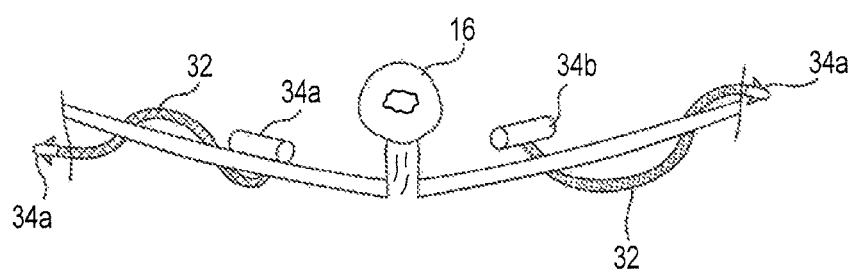

FIGS. 20-21 show certain embodiments of the present invention and devices 30 similar to that depicted in FIG. 16. The bulk anchor 34b (e.g., tubular, toggle (FIG. 26), flat, etc.) can be inserted through the supportive tissue, such as the endopelvic fascia, or it can reside under the supportive tissue, with the anchor 34a extending up through the tissue. As such, either of the anchors 34a, 34b can be positioned on the opposite side of the supportive tissue. Further, at least one of the anchors can serve to penetrate the supportive tissue at one or more locations along the tissue. For instance, certain embodiments of the device 30 can be utilized to weave or thread in and out of, and along, the tissue to provide a supportive undulating layout for the extension portion 32. This can facilitate attachment, better distribute pulling force on or along the tissue, and provide like support benefits.

Figure 22:
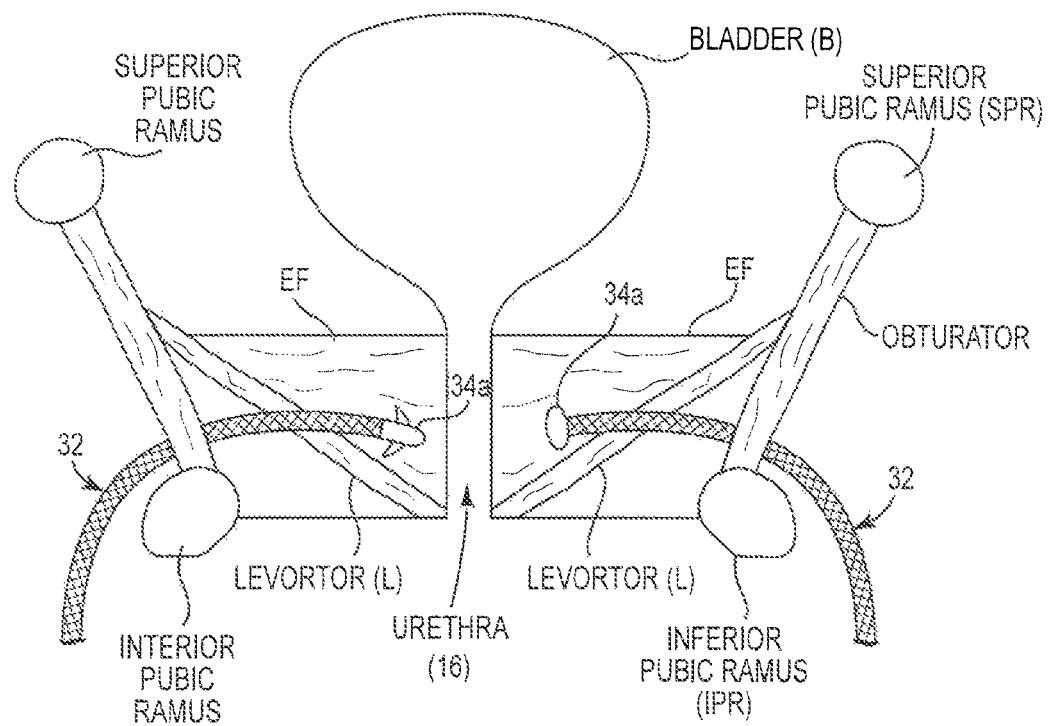
FIGS. 22-23 schematically show the implantation of implant devices through the obturator and into the lateral urethral support tissue in accordance with embodiments of the present invention.
Figure 23:
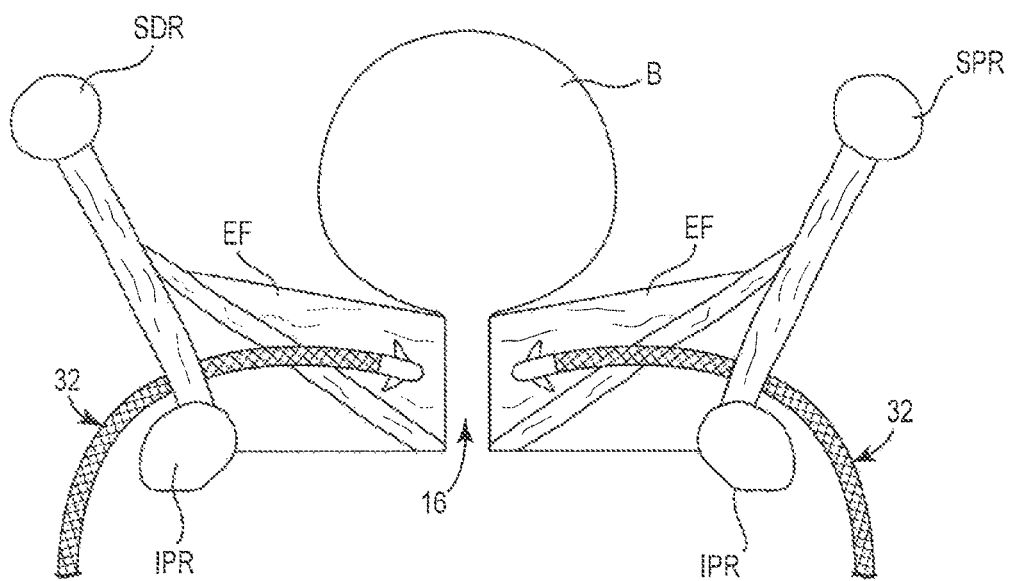

As shown in FIGS. 22-23, an outside-in implant approach can be employed for the device 30. Namely, a skin incision just inferior to where the adductor longus inserts into the pubic ramus can be created. Then, a first anchor 34a of the device 30 can be passed around the ischiopubic ramus and inserted through the obturator foramen and internus muscle and into the tissue lateral to the urethra, e.g., endopelvic fascia that supports the bladder neck and urethra. Once fixated, the device 30 can be pulled to provide tension along the extension portion 32 to augment and return the urethral support tissue to a correct anatomical position. At that point, the proximal opposing end of the device 30 and extension portion 32 can be anchored or otherwise positioned to maintain the tension on the device 30. Any of the needle and/or cannula introducer devices described herein can be employed to insert and deploy the device 30 within the patient. Such an embodiment of the device 30 can provide easier access and patient positioning, can eliminate the need for dissection under the urethra, and can be implanted while the patient is awake such that the device 30 can be selectively adjusted based on indications and movement of the patient. Embodiments of the base or end of the extension portion 32 on the entry side of the tissue could also be glued, sutured or otherwise fixated in or at the tissue using various known structures and techniques. Again, the device 30 can be implanted on either side of the urethra to provide bilateral support. FIG. 23 discloses a variation on this embodiment, with the extension portion 32 being constructed of a non-porous material, such as a suture, polymer material, string, etc.

Figure 24:
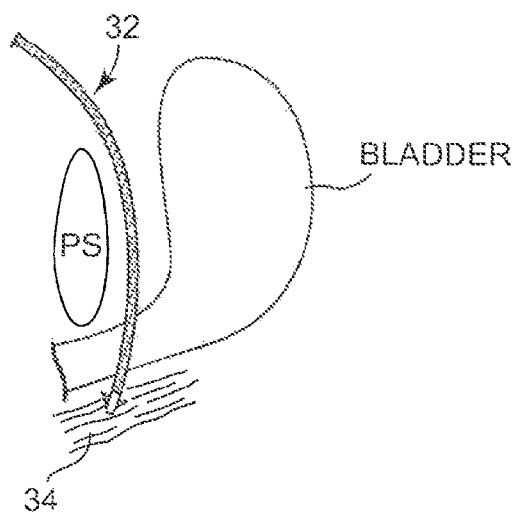
FIGS. 24-25 schematically show the retropubic implantation of implant devices to provide tensioning support for the lateral urethral support tissue in accordance with embodiments of the present invention.
Figure 25:
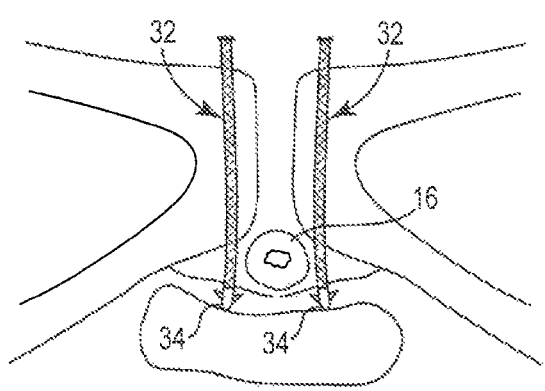
Figure 26:
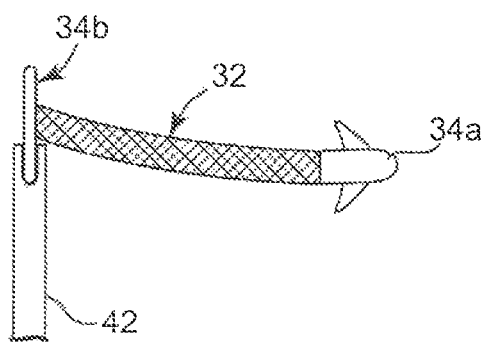
FIG. 26 shows an implant device having a toggle bolt anchor selectively engaged with an introducer device in accordance with embodiments of the present invention.

FIGS. 24-25 depict another embodiment of the implant device 30, introduced along a retropubic path, rather than a transobturator path. One or more skin incisions are generally created such that the device 30 can extend down on either, or both sides of the urethra, with at least one anchor 34 extending into the endopelvic fascia to the anterior vaginal wall. Like the other embodiments disclosed herein, fixation of the implant device 30 to the lateral supporting tissue of the urethra permits adjustment to return the supportive tissue to its correct anatomical position. Again, any of the anchors 34, extension portions 32 and introducer devices described herein can be employed with the embodiment of FIGS. 24-25.

Figure 27:
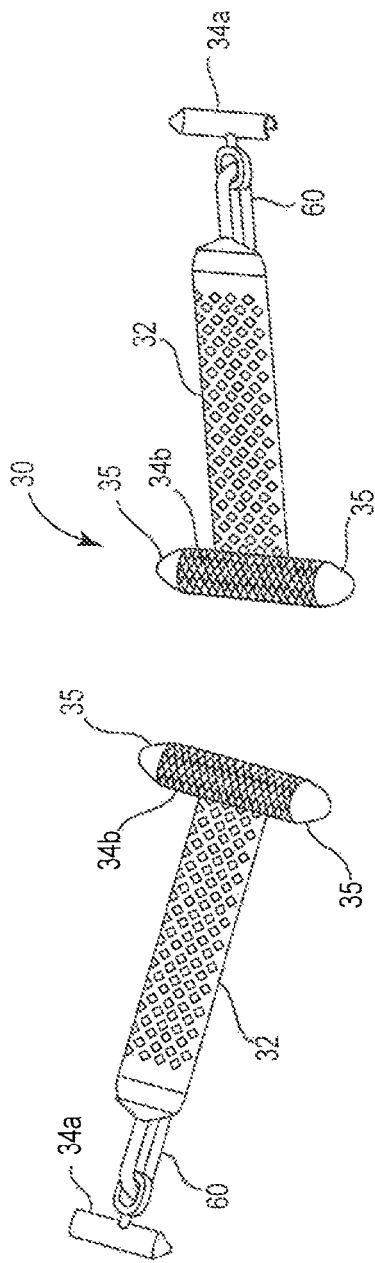
FIG. 27 shows implant devices having a toggle bolt anchor and a tubular base anchor in accordance with embodiments of the present invention.
Figure 28:
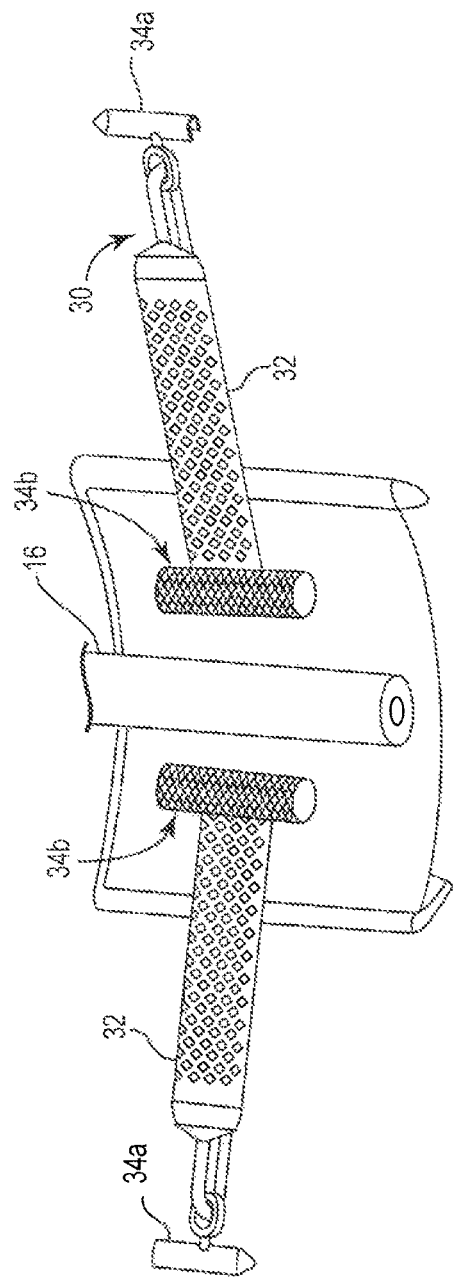
FIG. 28 schematically shows the implantation of the implant devices of FIG. 27 to provide support of the lateral urethral support tissue in accordance with embodiments of the present invention.
Figure 29:
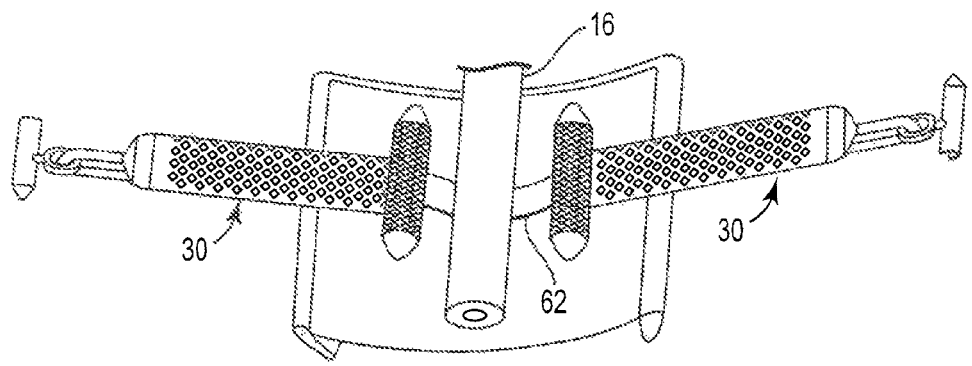
FIG. 29 shows an implant device having a toggle bolt anchor, a tubular base anchor, and an intermediate urethral cradling portion in accordance with embodiments of the present invention.

FIGS. 27-29 show various embodiments of the implant device 30 including engagement or anchoring portions 34a, 34b at each end of the extension portion 32 to provide lateral support of the urethra. The anchors can include any of the structures or features described herein. For example, one embodiment includes a toggle anchor 34a and a tubular (e.g., mesh) base anchor 34b. The tubular base 34b can include cap or other structure 35 provided at its ends. Like other embodiments of device 30, at least one of the anchors, such as tubular base 34b, can be engaged with lateral support tissue of the urethra such that the tissue can be tensioned or raised to remove slack. An adjustment member 60, e.g., rod, suture or like feature, can be included to provide selective adjustment of the device 30 to further facilitate tension control. For those embodiments including tubular engagement features 34b, the features 34b can be of a mesh construction to promote tissue fixation and in-growth. As shown in FIG. 29, this embodiment of the device 30 can further include an intermediate support 62 adapted for positioning under the urethra to provide additional support. The support 62 can be porous or non-porous, and any of the structures (e.g., anchors 34, support 62) can be constructed of re-absorbable or non-absorbable materials.

Figure 31:
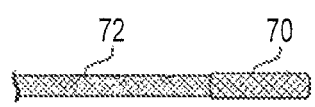
FIG. 31 shows an implant device having a tubular portion and a generally flat portion in accordance with embodiments of the present invention.
Figure 30:
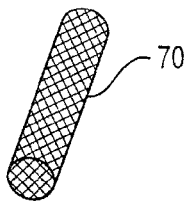
FIG. 30 shows a tubular implant device of device portion m accordance with embodiments of the present invention.
Figure 32:
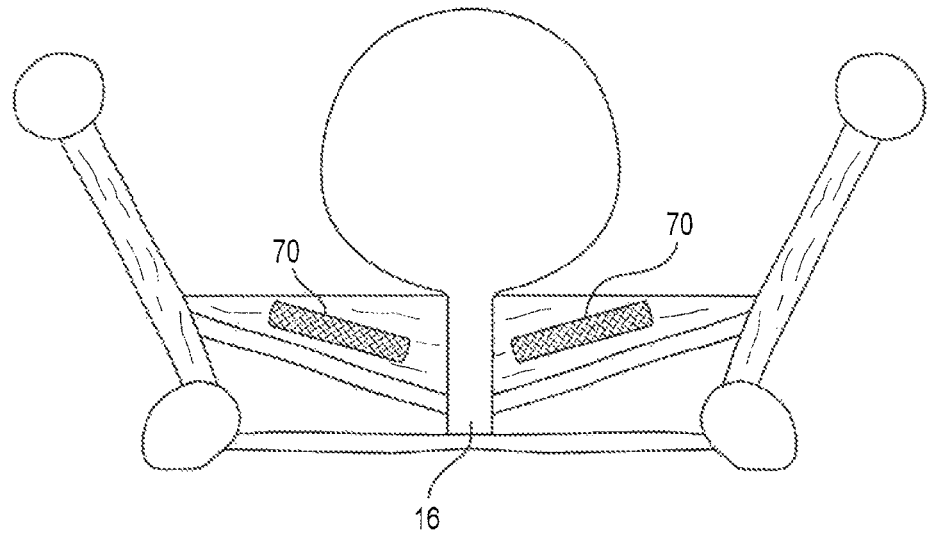
FIG. 32 schematically shows implantation of a tubular and/or flat implant device to provide tensioning support for the lateral urethral support tissue in accordance with embodiments of the present invention.
Figure 33:
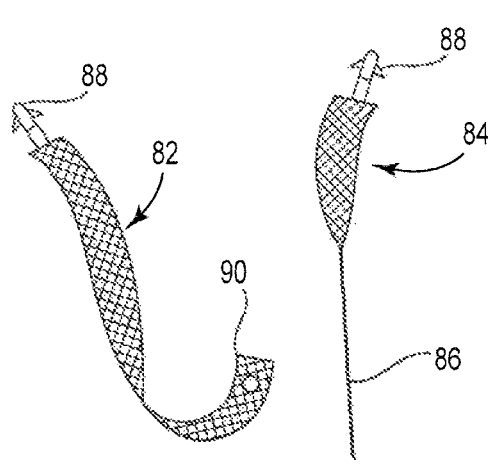
FIG. 33 shows an implant device having a first arm and a second arm in accordance with embodiments of the present invention.

FIGS. 30-32 depict implants 70 capable of fixation along a portion of the lateral urethral support tissue, e.g., the endopelvic fascia. These implants 70 can include one or more tubular and/or flat mesh structures 72 adapted for engagement with the support tissue to provide adjustment with and/or tension on the tissue. The structures 70, 72 can also be adapted for selective engagement with an introducer device 42 to facilitate insertion and deployment. The implants can be provided without anchors 34, wherein the construct and features (e.g., protrusions, mesh, abrasions, adhesives, fibers, etc.) of the implant can provide the attachment structures necessary to engage with and provide adjustable tension on the support tissue. Other embodiments can include anchors 34 to penetrate or engage the lateral tissue. Further, the implants 70 can be constructed of re-absorbable or non-absorbable materials.

The embodiments of FIGS. 33-38 can include an implant device 80 having a first extension arm 82, a second extension arm 84, and an adjustment member 86 provided with one or both of the extension arms 82, 84. The extension arms 82, 84 can include one or more anchors 88 at their respective ends. The arms 82, 84 can be constructed of a porous mesh, or other materials as described herein for the extension portion 32 of devices 30. Similarly, the anchors 88 can assume the configuration of any of the anchors 34 described herein. Components of the device 80, including the arms and adjustment member, can be constructed of compatible materials such as polypropylene, PGA, PLLA, mesh, braids, ropes, filaments, and the like.

Figure 34:
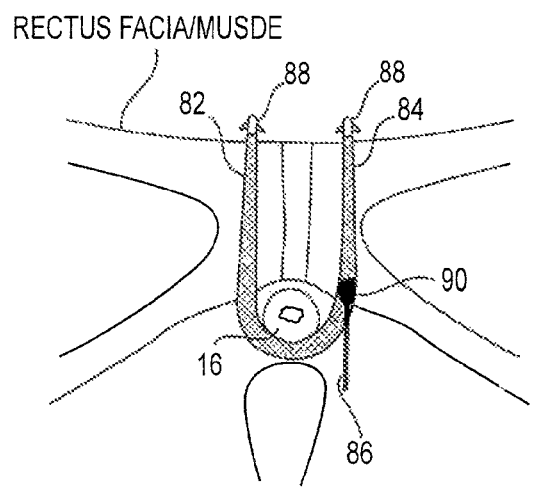
FIG. 34 schematically shows implantation of the implant device of FIG. 33 along a retropubic pathway in accordance with embodiments of the present invention.
Figure 35:
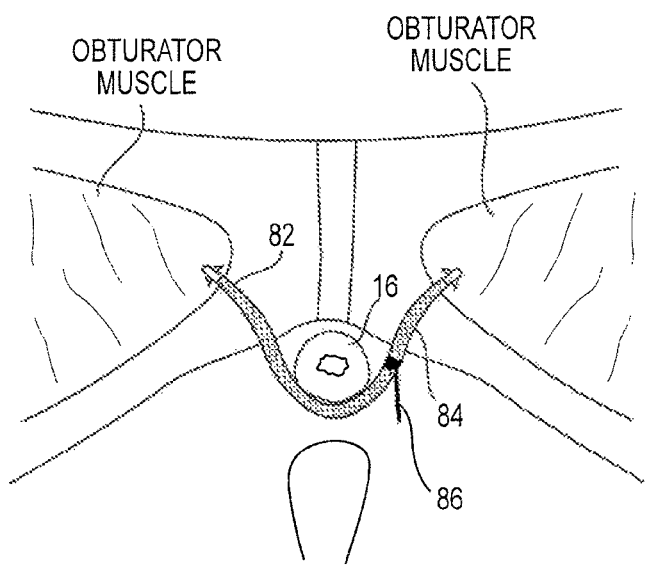
FIG. 35 schematically shows implantation of the implant device of FIG. 33 along a transobturator pathway in accordance with embodiments of the present invention.
Figure 36:
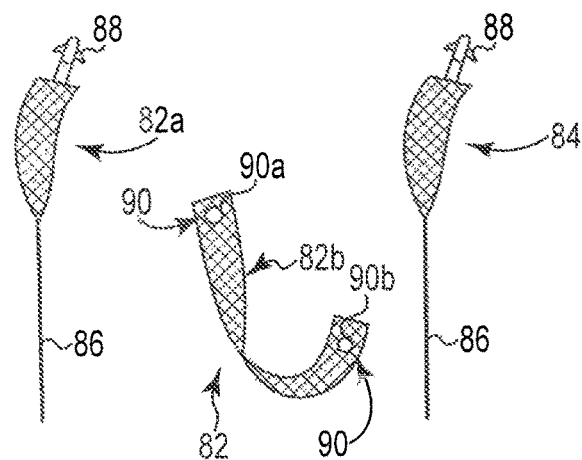
FIG. 36 shows an implant device having a first arm portions and second arm in accordance with embodiments of the present invention.
Figure 37:
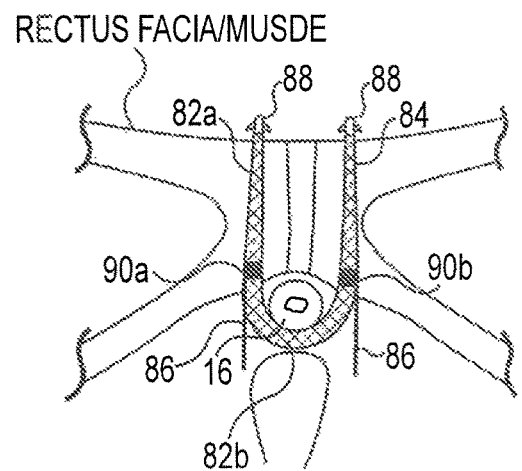
FIG. 37 schematically shows implantation of the implant device of FIG. 36 along a retropubic pathway in accordance with embodiments of the present invention.
Figure 38:
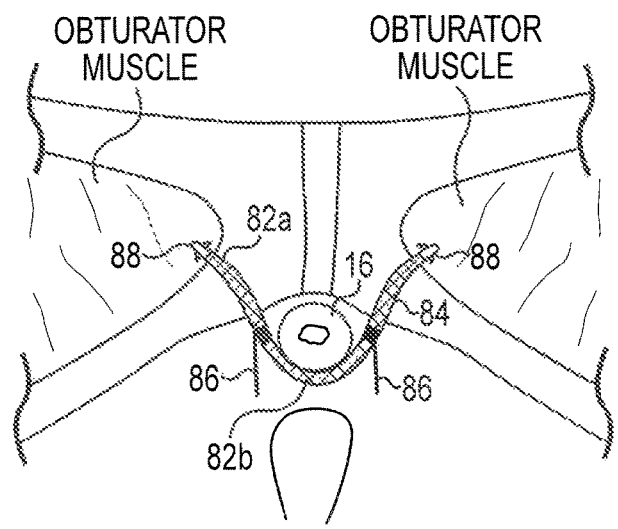
FIG. 38 schematically shows implantation of the implant device of FIG. 36 along a transobturator pathway in accordance with embodiments of the present invention.

Each of the arms 82, 84 (e.g., distinct or separate members) can be passed through one or more vaginal incisions, along a retropubic pathway, until the anchor 88 is secured in tissue, such as the rectus fascia/muscle, as shown in FIGS. 34 and 37. Further, a portion of either arm can extend under the urethra to provide cradling support (e.g., 82 or 82b). To tension the device 80, the member 86 (e.g., rod or polymer extension) of one or both of the arms 82, 84 can be inserted or engaged with an attachment or locking mechanism 90 (e.g., fastener, device, aperture, etc.) of the other arm or implant portion. The member 86 can then be slid along or through the locking mechanism 90 to engage the components until an appropriate tension is obtained. The remaining portion of the member 86 extending below the arms can be cut off and discarded. In other embodiments, each arm 82, 84 could include the member 86, or like adjustment mechanisms, to facilitate balanced or equal tensioning on either side of the urethra. For example, as shown in FIGS. 36-38, the first extension arm 82 includes separate portions 82a and 82b, with the portion 82a adapted for attachment to or through one of the apertures or locking mechanisms 90a of portion 82b, and the other of the apertures or locking mechanisms 90b of portion 82b adapted for receiving the second extension arm 84. As shown in FIGS. 35 and 38, the device 80 can be deployed, and the procedure performed along a transobturator pathway as well, with the anchors 88 being secured in the obturator muscle or like tissue on either side of the pelvis.

For those embodiments having an eyelet or aperture 90 to interconnect the arms 82, 84 or arm portions (e.g., 82a, 82b and 84), various tools (e.g., insertion and push tools), devices, mechanisms (e.g., grommets, and locking or adjustment elements), and techniques can be used to facilitate selective attachment and tensioning of the arms, including those disclosed in U.S. Patent Application Publication No. 2010/0261955, which is hereby incorporated by reference herein in its entirety. Embodiments of the present invention provide key advantages over fixed-length slings, thereby allowing treatment of a large range of patients with a wide range of anatomical dimensions with a single adjustable device.

Figure 39:
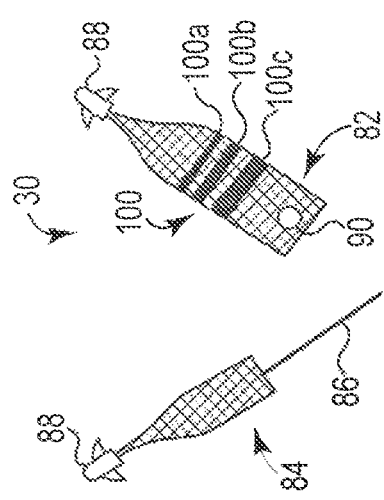
FIG. 39 shows an implant device having arm portions and adjustment indicia in accordance with embodiments of the present invention.
Figure 41:
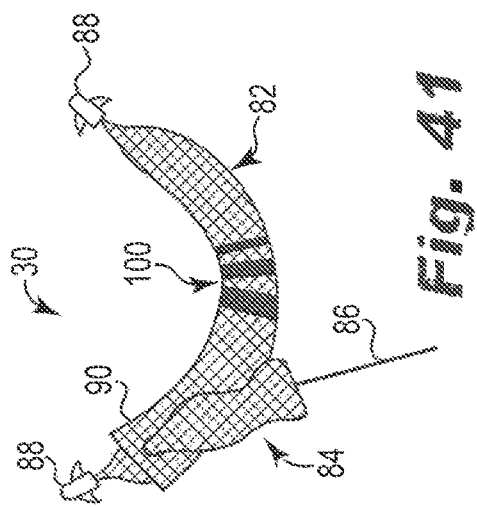
FIGS. 40-41 show slidable adjustment of the implant device of FIG. 39 in accordance with embodiments of the present invention.
Figure 40:
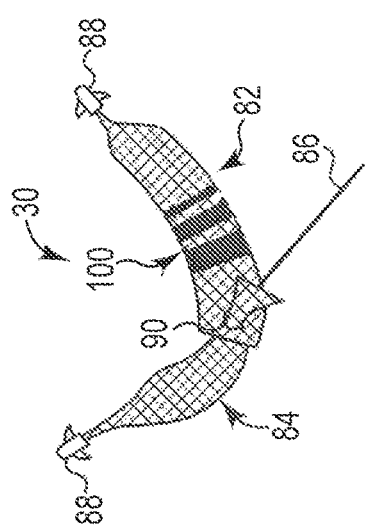

Various sling devices 30, including those having one or more extension arms 82, 84 (e.g., FIGS. 33-38), can include one or more indicia 100 to indicate adjustment, length and positioning thresholds and targets for the physician—e.g., large (100a), medium (100b), small (100c), etc., as shown in FIGS. 39-41. These indicia 100 can be included along any portion of the sling 30, including the portion intended for general central alignment with the anatomical structure to be supported. The indicia 100 can provide broad or granular adjustment indicators, for general alignment, or alignment with anatomical structures such as the urethra, bladder neck, or like structures. The number of indicia 100, and the visual representations, design and look, can vary greatly depending on the particular sling 30 use application. The indicia 100 can be provided to the corresponding portion of the sling 30 with compatible ink, polymer coating, coloring, molding, bonding, or by adding or otherwise including elements that are adapted to stand out (e.g., color, shape, size, design, etc.) along the designated sling portion.

A variety of materials may be used to form portions or components of the implants and devices 30, including Nitinol, polymers, elastomers, porous mesh, thermoplastic elastomers, metals, ceramics, springs, wires, plastic tubing, and the like. The systems, components and methods may have a number of suitable configurations known to one of ordinary skill in the art after reviewing the disclosure provided herein.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

What is claimed is:

1. An elongate implantable incontinence sling system, comprising:
    a tissue support portion having a first eyelet and a second eyelet;
    a first extension arm having a first anchor portion and a first extension member, at least a length of the first extension arm is adapted to slide through the first eyelet of the tissue support portion, the first extension member having a first portion of a first construct and a second portion of a second construct different than the first construct of the first extension arm; and
    a second extension arm having a second anchor portion and a second extension member, at least a length of the second extension arm adapted to slide through the second eyelet of the tissue support portion, the second extension member having a first portion of a first construct and a second portion of a second construct different than the first construct of the second extension arm.

2. The sling system of claim 1, wherein the first construct includes a mesh material.

3. The sling system of claim 1, wherein at least a portion of the second extension arm is constructed of a mesh material.

4. The sling system of claim 1, wherein the second extension member includes an extension rod.

5. The sling system of claim 4, wherein the extension rod is a polymer extension rod.

6. The sling system of claim 1, further including a grommet adapted to engage at least one of the first and second eyelets to facilitate attachment of the first extension arm or the second extension arm.

7. The sling system of claim 1, further including one or more alignment indicia provided along a portion of the tissue support portion.

8. The sling system of claim 7, wherein the one or more indicia includes three indicia adapted to guide placement of the elongate sling relative to tissue targeted for support.

9. The sling system of claim 1, wherein the anchor portion of at least one of the first and second extension arms is adapted to engage with obturator tissue.

10. The sling system of claim 1, wherein the anchor portion of at least one of the first and second extension arms is adapted to engage with rectus fascia.

11. The sling system of claim 1, wherein the tissue support portion spans under and provides support to the urethra.

12. An elongate implantable incontinence sling system, comprising:
    a tissue support portion having a first eyelet and a second eyelet;
    a first extension arm having a first anchor portion, a first portion having a first width, and a second portion having a second width smaller than the first width, at least a length of the first extension arm being adapted to slide through the first eyelet of the tissue support portion; and
    a second extension arm having a second anchor portion, a first portion having a first width, and a second portion having a second width smaller than the first width, at least a length of the second extension arm being adapted to slide through the second eyelet of the tissue support portion.

13. The sling system of claim 12, wherein the first portion of the first extension arm is constructed of a mesh material.

14. The sling system of claim 12, wherein the first portion of the second extension arm is constructed of a mesh material.

15. The sling system of claim 12, wherein the second portion of the first extension arm includes an extension rod.

16. The sling system of claim 12, wherein the extension rod is a polymer extension rod.

17. The sling system of claim 12, further including a grommet adapted to engage at least one of the first and second eyelets to facilitate attachment of the first extension arm or the second extension arm.

18. The sling system of claim 12, further including one or more alignment indicia provided along a portion of the tissue support portion.

19. The sling system of claim 1, wherein the second construct includes a rod.

20. The sling system of claim 19, wherein the rod is a polymer rod.

* * * * *